US008367375B2

(12) United States Patent
Kodama et al.

(10) Patent No.: US 8,367,375 B2
(45) Date of Patent: Feb. 5, 2013

(54) METHODS FOR PRODUCING HUMAN CERAMIDE USING YEAST TRANSFORMANTS

(75) Inventors: Yukiko Kodama, Mishima-gun (JP); Hiroaki Okuhara, Mishima-gun (JP); Koichi Funato, Higashi-Hiroshima (JP)

(73) Assignees: Suntory Holdings Limited, Osaka-shi, Osaka (JP); Hiroshima University, Higashi-Hiroshima-shi, Hiroshima (JP)

( * ) Notice: Subject to any disclaimer, the term of this patent is extended or adjusted under 35 U.S.C. 154(b) by 243 days.

(21) Appl. No.: 12/663,232

(22) PCT Filed: May 20, 2008

(86) PCT No.: PCT/JP2008/059241
§ 371 (c)(1),
(2), (4) Date: Dec. 4, 2009

(87) PCT Pub. No.: WO2008/149665
PCT Pub. Date: Dec. 11, 2008

(65) Prior Publication Data
US 2010/0304467 A1  Dec. 2, 2010

(30) Foreign Application Priority Data
Jun. 5, 2007  (JP) ................................. 2007-149657

(51) Int. Cl.
C12P 21/00  (2006.01)
C12N 1/19  (2006.01)
(52) U.S. Cl. ................................... 435/71.1; 435/254.2
(58) Field of Classification Search .......................... None
See application file for complete search history.

(56) References Cited

U.S. PATENT DOCUMENTS
2004/0106193 A1*  6/2004  Kay et al. ..................... 435/320.1
2009/0325247 A1  12/2009  Kodama et al.

FOREIGN PATENT DOCUMENTS
WO  WO-2007066595 A1  6/2007

OTHER PUBLICATIONS

Kim et al. Accumulation of phosphorylated sphingoid long chain bases results in cell growth inhibition in Saccharomyces cerevisiae. Genetics. Dec. 2000;156(4):1519-29.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Genbank accession No. Q15121, 2012.*
Genbank accession No. P38992, 2012.*
Genbank accession No. Q12246, 2012.*
Genbank accession No. Q03529, 2012.*
Ternes, P. et al., "Identification and Characterization of a Sphingolipid delta4-Desaturase Family", The Journal of Biological Chemistry, 2002, vol. 277, No. 28, pp. 25512-25518.
Funato K. et al., "Biosynthesis and Trafficking of Sphingolipids in the Yeast Saccharomyces cerevisiae", Biochemistry, 2002, vol. 41, No. 51, pp. 15105-15114, XP003013885.
Haak D. et al., "Hydroxylation of Saccharomyces cerevisiae Ceramides Requires Sur2p and Scs7p", The Journal of Biological Chemistry, 1997, vol. 272, No. 47, Issue of Nov. 21, pp. 29704-29710, XP002119022.
Sims K. J. et al., "Yeast sphingolipid metabolism: clues and connections", Biochem. Cell Biol., vol. 82, 2004, pp. 45-61, XP003013888.
Merrill A.H., "De Novo Sphingolipid Biosynthesis: A Necessary but Dangerous, Pathway", The Journal of Biological Chemistry, 2002, vol. 277, No. 29, pp. 25843-25846, XP008125162.
Funato K. et al., "Lcb4p Is a Key Regulator of Ceramide Synthesis from Exogenous Long Chain Sphingoid Base in Saccharomyces cerevisiae' ", The Journal of Biological Chemistry, 2003, vol. 278, No. 9, pp. 7325-7334, XP008125163.
Desfarges, L. et al., "Yeast Mutants Affected in Viability upon Starvation Have a Modified Phospholipid Composition", Yeast, vol. 9; pp. 267-277, 1993.
Mao, C. et al., "Cloning and Characterization of a Saccharomyces cerevisiae Alkaline Ceramidase with Specificity for Dihydroceramide", The Journal of Biological Chemistry, vol. 275, pp. 31369-31378, 2000.
Sawai, H. et al., "Identification of ISC1 (YER019w) as Inositol Phosphosphingolipid Phospholipase C in Saccharomyces cerevisiae", The Journal of Biological Chemistry, 2000, vol. 275, No. 40, pp. 39793-39798.
International Search Report mailed Jul. 8, 2008, issued in International Application No. PCT/JP2008/059241 filed May 20, 2008.
Funato et al., "Sphingolipid Biosynthesis and Traffic in Yeast," Seikagaku, vol. 74, No. 4, pp. 317-321, (2002) (w/ partial English translation), p. 1-3 only.
Office Action dated Jan. 6, 2011 issued in Japanese Application No. 2005-351366 (w/ English translation).
Supplementary European Search Report dated Sep. 19, 2012; Application No. EP08764400.1.
Pewzner-Jung Yael, et al., "When do lasses (longevity assurance genes) become CerS (ceramide synthases)?Insights into the regulation of ceramide synthesis", Journal of Biological Chemistry, vol. 281, No. 35, Sep. 2006, pp. 25001-25005, XP002681945, ISSN: 0021-9258 (the whole document).
Guillas Isabelle, et al., "Human homologues of LAG1 reconstitute acyl-CoA-dependent ceramide synthesis in yeast.", Journal of Biological Chemistry, vol. 276, No. 39, Sep. 26, 2003, pp. 37083-37091, XP002681946, ISSN: 0021-9258 (the whole document).

Primary Examiner — Michele K Joike
(74) Attorney, Agent, or Firm — Drinker Biddle & Reath LLP

(57) ABSTRACT

The present invention provides a method for producing human ceramide in a yeast cell.
The method of the present invention comprises:
1) introducing the sphingoid Δ4-desaturase gene (DES1) by transformation of the yeast cell;
2) abolishing the expression of the yeast sphinganine C4-hydroxylase gene (SUR2) by transformation of the yeast cell; and
3) abolishing the expression of the yeast sphingoid base kinase gene (LCB4) by transformation of the yeast cell.

2 Claims, 5 Drawing Sheets

Difference of the synthetic/metabolic pathway for sphingolipids between yeast and animal cells

Analyses of sphingoid bases by TLC, HPLC

SEQUENCE LISTING

```
<160> NUMBER OF SEQ ID NOS: 31

<210> SEQ ID NO 1
<211> LENGTH: 972
<212> TYPE: DNA
<213> ORGANISM: Homo sapiens

<400> SEQUENCE: 1
atggggagcc gcgtctcgcg ggaagacttc gagtgggtct acaccgacca gccgcacgcc      60
gaccggcgcc gggagatcct ggcaaagtat ccagagataa agtccttgat gaaacctgat     120
cccaatttga tatggattat aattatgatg gttctcaccc agttgggtgc attttacata     180
gtaaaagact tggactggaa atgggtcata tttggggcct atgcgtttgg cagttgcatt     240
aaccactcaa tgactctggc tattcatgag attgcccaca atgctgcctt tggcaactgc     300
aaagcaatgt ggaatcgctg gtttggaatg tttgctaatc ttcctattgg gattccatat     360
tcaatttcct ttaagaggta tcacatggat catcatcggt accttggagc tgatggcgtc     420
gatgtagata ttcctaccga ttttgagggc tggttcttct gtaccgcttt cagaaagttt     480
atatgggtta ttcttcagcc tctctttat gcctttcgac ctctgttcat caaccccaaa     540
ccaattacgt atctggaagt tatcaatacc gtggcacagg tcactttga cattttaatt     600 tattacttt tgggaattaa atccttagtc tacatgttgg cagcatcttt acttggcctg     660
ggtttgcacc caatttctgg acatttata gctgagcatt acatgttctt aaagggtcat     720
gaaacttact catattatgg gcctctgaat ttacttacct tcaatgtggg ttatcataat     780
gaacatcatg atttcccccaa cattcctgga aaaagtcttc cactggtgag gaaaatagca     840
gctgaatact atgacaacct ccctcactac aattcctgga taaagtact gtatgatttt     900 gtgatggatg atacaataag tccctactca agaatgaaga ggcaccaaaa aggagagatg     960
gtgctggagt aa                                                         972

<210> SEQ ID NO 2
<211> LENGTH: 323
<212> TYPE: PRT
<213> ORGANISM: Homo sapiens

<400> SEQUENCE: 2

Met Gly Ser Arg Val Ser Arg Glu Asp Phe Glu Trp Val Tyr Thr Asp
1               5                   10                  15

Gln Pro His Ala Asp Arg Arg Glu Ile Leu Ala Lys Tyr Pro Glu
            20                  25                  30

Ile Lys Ser Leu Met Lys Pro Asp Pro Asn Leu Ile Trp Ile Ile
        35                  40                  45

Met Met Val Leu Thr Gln Leu Gly Ala Phe Tyr Ile Val Lys Asp Leu
    50                  55                  60

Asp Trp Lys Trp Val Ile Phe Gly Ala Tyr Ala Phe Gly Ser Cys Ile
65                  70                  75                  80

Asn His Ser Met Thr Leu Ala Ile His Glu Ile Ala His Asn Ala Ala
```

|   |   |   |   |   | 85  |   |   |   |   | 90  |   |   |   |   | 95  |   |
|---|---|---|---|---|-----|---|---|---|---|-----|---|---|---|---|-----|---|

Phe Gly Asn Cys Lys Ala Met Trp Asn Arg Trp Phe Gly Met Phe Ala
              100                 105                 110

Asn Leu Pro Ile Gly Ile Pro Tyr Ser Ile Ser Phe Lys Arg Tyr His
            115                 120                 125

Met Asp His His Arg Tyr Leu Gly Ala Asp Gly Val Asp Val Asp Ile
        130                 135                 140

Pro Thr Asp Phe Glu Gly Trp Phe Phe Cys Thr Ala Phe Arg Lys Phe
145                 150                 155                 160

Ile Trp Val Ile Leu Gln Pro Leu Phe Tyr Ala Phe Arg Pro Leu Phe
                165                 170                 175

Ile Asn Pro Lys Pro Ile Thr Tyr Leu Glu Val Ile Asn Thr Val Ala
            180                 185                 190

Gln Val Thr Phe Asp Ile Leu Ile Tyr Tyr Phe Leu Gly Ile Lys Ser
        195                 200                 205

Leu Val Tyr Met Leu Ala Ala Ser Leu Leu Gly Leu Gly Leu His Pro
    210                 215                 220

Ile Ser Gly His Phe Ile Ala Glu His Tyr Met Phe Leu Lys Gly His
225                 230                 235                 240

Glu Thr Tyr Ser Tyr Tyr Gly Pro Leu Asn Leu Leu Thr Phe Asn Val
                245                 250                 255

Gly Tyr His Asn Glu His His Asp Phe Pro Asn Ile Pro Gly Lys Ser
            260                 265                 270

Leu Pro Leu Val Arg Lys Ile Ala Ala Glu Tyr Tyr Asp Asn Leu Pro
        275                 280                 285

His Tyr Asn Ser Trp Ile Lys Val Leu Tyr Asp Phe Val Met Asp Asp
    290                 295                 300

Thr Ile Ser Pro Tyr Ser Arg Met Lys Arg His Gln Lys Gly Glu Met
305                 310                 315                 320

Val Leu Glu

<210> SEQ ID NO 3
<211> LENGTH: 1420
<212> TYPE: DNA
<213> ORGANISM: Saccharomyces cerevisiae

<400> SEQUENCE: 3
ctccggcttc tgcggttttt cttagtcttt ccgcaccaat tttcacagaa aaatttcttt     60
ttgggttact aaaaatttct tgtttgctat tgtcttgatt tatttcactc tttcttcatc    120
ctgctgcgct gttgttgccg cattttttcgt ttcgtgtttt gggattataa agaagtaac    180
gatttacata tcttctattc ccttgcattt actccgggtc ttcgtcttta ctgtttggtc    240
tgggtatttc taacattcta gtccgaagag ggtgtatacg aaaagaaaat atacgatgaa    300
cgtaacatcg aatgcaactg cagccggttc ctttccacta gcatttggtc tcaagacctc    360
atttgggttt atgcactatg ccaaggcccc tgccattaat ttacgcccca ggaatccttt    420
gctgccggaa atgagtgatg gtgtgctggc cttggttgcg ccggttgttg cctactgggc    480
gttgtctggt atattccatg taatagacac tttccatctg gctgagaagt acagaattca    540
tccgagcgaa gaggttgcca agaggaacaa ggcgtcgaga atgcatgttt tccttgaagt    600
gattctacaa catatcatac agaccattgt tggccttatc tttatgcact cgagccgat    660
ctacatgact gggtttgaag aaaatgccat gtggaagctt cgtgcagacc ttcctcggat    720
tattccagat gccgctattt attacggcta tatgtacgga atgtccgctt tgaagatctt    780

```
tgcaggcttt ttattcgttg atacatggca atacttttg catagattga tgcatatgaa      840
taagacctta tacaaatggt tccactctgt tcatcatgaa ctatacgtgc catatgctta      900
cggtgctctt ttcaacaatc ctgttgaggg cttcttgtta gatactttgg gaaccggtat      960
tgccatgacg ttaactcatt tgactcacag agagcaaatc attcttttta cctttgccac     1020
catgaagact gtcgatgacc actgtgggta tgctttgcca cttgacccat ccaatggct      1080 tttccctaat aacgctgtct atcacgatat ccaccaccag caatttggta tcaagacgaa     1140
ctttgctcaa ccattttca ctttctggga caatttgttc caaactaact ttaaagggtt     1200
tgaagaatat caaaagaagc aaagacgtgt caccatcgac aagtacaaag agttttgca     1260 agagagagaa ttggaaaaga aggagaaact caaaaacttc aaagctatga atgctgctga     1320
aaatgaagta aagaaagaga aataacccctt ttgcatacct cccgttcaat tgctgggtaa     1380
aggcaatgtc tccgacttcc cacgtttgta tttattatcc                            1420

<210> SEQ ID NO 4
<211> LENGTH: 1920
<212> TYPE: DNA
<213> ORGANISM: Saccharomyces cerevisiae

<400> SEQUENCE: 4
cctgaaaagg cttcagcgct gcatacatag acatatacac atcacacgta catacacgaa       60
aagatagctt tcatgctcac aaagctacgt tccccacaga atatttccca ggacaacagg      120
gaaagttgga caaacaccaa acttctcata atacaatagc cgaaaacagt cttgcttttg      180
ataaagagag ctttctgcgg ccggaagaaa atgtgcctat tccgcggggc cgttccgcgc      240
agaaactacc gcacgacgtc ggaaatataa cggggttttg cgcggattta ctgacgtgtg      300
acatcttttc gcagttaatt ttttttttcaa tttggaaccg tataagaaca gaggtattag      360
atagtagaag ctattgtgtc tattgtcttt gattagtttt ttttttctatt gttatcgtgg      420 caggcactaa aagcggtggt aagctaaaac tagtacgaag atgtcgacta atacttccaa      480
gacttttgga ctgttttcaa aaaagacggt acaagaacac aatactgcca atgactgctg      540
ggtcacttat caaaacagaa agatttatga cgtgaccagg tttttgagcg aacaccctgg      600
tggtgacgag tccatcttgg actatgctgg taaggacatt actgagatca tgaaagactc      660
agatgtgcat gaacacagcg actccgcgta tgaaatcctt gaggacgaat atttgattgg      720
ttacttggca actgacgaag aggcagcgag attgttgact aacaagaacc ataaggttga      780
agtgcagttg tcagctgacg gtactgagtt tgactccact acttttgtaa aggagttgcc      840
cgccgaggag aaactaagta ttgctacgga ctacagtaac gactacaaaa agcataaatt      900
tttggatctg aaccgtcctt tgctgatgca gattctgcgt agtgatttca agaaagattt      960
ttacgttgac caaatccata gaccaagaca ttacggtaag gggtctgccc cgctatttgg     1020
taatttcttg gaaccattaa ctaaaacagc ttggtgggtt gttccagttg cttggttgcc     1080
tgtagttgtg taccacatgg gtgttgcttt gaagaacatg aaccagctat ttgcatgttt     1140
cttgttctgt gtcggtgtct ttgttggac tttgattgaa tacggtcttc accgtttcct     1200
atttcatttc gatgattggt tacctgaaag taacatcgca ttcgccacac attttctact     1260
acatggttgc catcattact tgcccatgga caagtaccgt ttagttatgc cacctactct     1320
gttcgtcatc ctttgtgctc cattttacaa gttggtattt gctctgctgc cactttattg     1380
ggcttacgct ggttttgctg gcggtctttt cggttatgtc tgttatgacg aatgtcattt     1440
cttcttgcac cactctaaat tgcctccctt catgcgtaag ttgaaaaaat atcacctgga     1500
```

```
acatcattat aaaaactacc aactgggatt tggcgtcaca tcctggtttt gggacgaagt    1560
ttttggcacc tacttaggcc ccgatgcccc attgtccaaa atgaaatatg aataattatt    1620
ggtcagcctc gtccaaaatt gtcaacctag gaaaacaac  attacgagca atgaaatctt    1680
gagcaaagtt cttttctgcg acatatttat ttcaaatctt tatttatatt attatatgta    1740
actacgtata tatacataca catggaatgg aatcatagat gaaatcgatg aacaagcacg    1800
ttatttctta aacgaatatc caatcgatga cgactatacg aaaaagcggc ctcaaaaaag    1860
aaccgaattg acaggtacat ttttctttca cagatcaggt tggcaaaaaa atactaaccg    1920
```

<210> SEQ ID NO 5
<211> LENGTH: 1050
<212> TYPE: DNA
<213> ORGANISM: Saccharomyces cerevisiae

<400> SEQUENCE: 5

```
atgaacgtaa catcgaatgc aactgcagcc ggttcctttc cactagcatt tggtctcaag      60
acctcatttg ggtttatgca ctatgccaag gcccctgcca ttaatttacg ccccaaggaa     120
tccttgctgc cggaaatgag tgatggtgtg ctggccttgg ttgcgccggt tgttgcctac     180
tgggcgttgt ctggtatatt ccatgtaata gacactttcc atctggctga aagtacaga      240 attcatccga gcgaagaggt tgccaagagg aacaaggcgt cgagaatgca tgttttcctt     300
gaagtgattc tacaacatat catacagacc attgttggcc ttatctttat gcacttcgag     360
ccgatctaca tgactgggtt tgaagaaaat gccatgtgga agcttcgtgc agaccttcct     420
cggattattc cagatgccgc tatttattac ggctatatgt acggaatgtc cgctttgaag     480
atctttgcag cttttttatt cgttgataca tggcaatact ttttgcatag attgatgcat     540
atgaataaga ccttatacaa atggttccac tctgttcatc atgaactata cgtgccatat     600
gcttacggtg ctctttttcaa caatcctgtt gagggcttct tgttagatac tttgggaacc     660
ggtattgcca tgacgttaac tcatttgact cacagagagc aaatcattct tttaccttt      720 gccaccatga agactgtcga tgaccactgt gggtatgctt tgccacttga cccattccaa     780
tggcttttcc ctaataacgc tgtctatcac gatatccacc accagcaatt tggtatcaag     840
acgaactttg ctcaaccatt tttcactttc tgggacaatt tgttccaaac taactttaaa     900
gggtttgaag aatatcaaaa gaagcaaaga cgtgtcacca tcgacaagta caaagagttt     960
ttgcaagaga gagaattgga aaagaaggag aaactcaaaa acttcaaagc tatgaatgct    1020
gctgaaaatg aagtaaagaa agagaaataa                                      1050
```

<210> SEQ ID NO 6
<211> LENGTH: 349
<212> TYPE: PRT
<213> ORGANISM: Saccharomyces cerevisiae

<400> SEQUENCE: 6

```
Met Asn Val Thr Ser Asn Ala Thr Ala Ala Gly Ser Phe Pro Leu Ala
1               5                   10                  15

Phe Gly Leu Lys Thr Ser Phe Gly Phe Met His Tyr Ala Lys Ala Pro
            20                  25                  30

Ala Ile Asn Leu Arg Pro Lys Glu Ser Leu Leu Pro Glu Met Ser Asp
        35                  40                  45

Gly Val Leu Ala Leu Val Ala Pro Val Val Ala Tyr Trp Ala Leu Ser
    50                  55                  60

Gly Ile Phe His Val Ile Asp Thr Phe His Leu Ala Glu Lys Tyr Arg
65                  70                  75                  80
```

Ile His Pro Ser Glu Glu Val Ala Lys Arg Asn Lys Ala Ser Arg Met
             85                  90                  95

His Val Phe Leu Glu Val Ile Leu Gln His Ile Ile Gln Thr Ile Val
            100                 105                 110

Gly Leu Ile Phe Met His Phe Glu Pro Ile Tyr Met Thr Gly Phe Glu
            115                 120                 125

Glu Asn Ala Met Trp Lys Leu Arg Ala Asp Leu Pro Arg Ile Ile Pro
        130                 135                 140

Asp Ala Ala Ile Tyr Tyr Gly Tyr Met Tyr Gly Met Ser Ala Leu Lys
145                 150                 155                 160

Ile Phe Ala Gly Phe Leu Phe Val Asp Thr Trp Gln Tyr Phe Leu His
                165                 170                 175

Arg Leu Met His Met Asn Lys Thr Leu Tyr Lys Trp Phe His Ser Val
            180                 185                 190

His His Glu Leu Tyr Val Pro Tyr Ala Tyr Gly Ala Leu Phe Asn Asn
        195                 200                 205

Pro Val Glu Gly Phe Leu Leu Asp Thr Leu Gly Thr Gly Ile Ala Met
    210                 215                 220

Thr Leu Thr His Leu Thr His Arg Glu Gln Ile Ile Leu Phe Thr Phe
225                 230                 235                 240

Ala Thr Met Lys Thr Val Asp Asp His Cys Gly Tyr Ala Leu Pro Leu
                245                 250                 255

Asp Pro Phe Gln Trp Leu Phe Pro Asn Asn Ala Val Tyr His Asp Ile
            260                 265                 270

His His Gln Gln Phe Gly Ile Lys Thr Asn Phe Ala Gln Pro Phe Phe
        275                 280                 285

Thr Phe Trp Asp Asn Leu Phe Gln Thr Asn Phe Lys Gly Phe Glu Glu
    290                 295                 300

Tyr Gln Lys Lys Gln Arg Arg Val Thr Ile Asp Lys Tyr Lys Glu Phe
305                 310                 315                 320

Leu Gln Glu Arg Glu Leu Glu Lys Lys Glu Lys Leu Lys Asn Phe Lys
                325                 330                 335

Ala Met Asn Ala Ala Glu Asn Glu Val Lys Lys Glu Lys
            340                 345

<210> SEQ ID NO 7
<211> LENGTH: 1155
<212> TYPE: DNA
<213> ORGANISM: Saccharomyces cerevisiae

<400> SEQUENCE: 7

```
atgtcgacta tacttccaa  gactttggaa ctgttttcaa aaaagacggt acaagaacac      60
aatactgcca atgactgctg ggtcacttat caaaacagaa agatttatga cgtgaccagg     120
tttttgagcg aacaccctgg tggtgacgag tccatcttgg actatgctgg taaggacatt     180
actgagatca tgaaagactc agatgtgcat gaacacagcg actccgcgta tgaaatcctt     240
gaggacgaat atttgattgg ttacttggca actgacgaag aggcagcgag attgttgact     300
aacaagaacc ataaggttga agtgcagttg tcagctgacg gtactgagtt tgactccact     360
acttttgtaa aggagttgcc cgccgaggag aaactaagta ttgctacgga ctacagtaac     420
gactacaaaa agcataaatt tttggatctg aaccgtcctt tgctgatgca gattctgcgt     480
agtgatttca agaaagattt ttacgttgac caaatcccta gaccaagaca ttacggtaag     540
gggtctgccc cgctatttgg taatttcttg gaaccattaa ctaaaacagc ttggtgggtt     600
```

-continued

```
gttccagttg cttggttgcc tgtagttgtg taccacatgg gtgttgcttt gaagaacatg    660
aaccagctat ttgcatgttt cttgttctgt gtcggtgtct ttgtttggac tttgattgaa    720
tacggtcttc accgtttcct atttcatttc gatgattggt tacctgaaag taacatcgca    780
ttcgccacac attttctact acatggttgc catcattact tgcccatgga caagtaccgt    840
ttagttatgc cacctactct gttcgtcatc ctttgtgctc catttacaa gttggtattt     900 gctctgctgc cactttattg ggcttacgct ggttttgctg gcggtctttt cggttatgtc    960
tgttatgacg aatgtcattt cttcttgcac cactctaaat tgcctcccctt catgcgtaag  1020 ttgaaaaaat atcacctgga acatcattat aaaaactacc aactgggatt tggcgtcaca   1080
tcctggtttt gggacgaagt ttttggcacc tacttaggcc ccgatgcccc attgtccaaa   1140
atgaaatatg aataa                                                    1155
```

<210> SEQ ID NO 8
<211> LENGTH: 384
<212> TYPE: PRT
<213> ORGANISM: Saccharomyces cerevisiae

<400> SEQUENCE: 8

```
Met Ser Thr Asn Thr Ser Lys Thr Leu Glu Leu Phe Ser Lys Lys Thr
  1               5                  10                  15

Val Gln Glu His Asn Thr Ala Asn Asp Cys Trp Val Thr Tyr Gln Asn
             20                  25                  30

Arg Lys Ile Tyr Asp Val Thr Arg Phe Leu Ser Glu His Pro Gly Gly
         35                  40                  45

Asp Glu Ser Ile Leu Asp Tyr Ala Gly Lys Asp Ile Thr Glu Ile Met
     50                  55                  60

Lys Asp Ser Asp Val His Glu His Ser Asp Ser Ala Tyr Glu Ile Leu
 65                  70                  75                  80

Glu Asp Glu Tyr Leu Ile Gly Tyr Leu Ala Thr Asp Glu Glu Ala Ala
                 85                  90                  95

Arg Leu Leu Thr Asn Lys Asn His Lys Val Glu Val Gln Leu Ser Ala
            100                 105                 110

Asp Gly Thr Glu Phe Asp Ser Thr Thr Phe Val Lys Glu Leu Pro Ala
        115                 120                 125

Glu Glu Lys Leu Ser Ile Ala Thr Asp Tyr Ser Asn Asp Tyr Lys Lys
    130                 135                 140

His Lys Phe Leu Asp Leu Asn Arg Pro Leu Leu Met Gln Ile Leu Arg
145                 150                 155                 160

Ser Asp Phe Lys Lys Asp Phe Tyr Val Asp Gln Ile His Arg Pro Arg
                165                 170                 175

His Tyr Gly Lys Gly Ser Ala Pro Leu Phe Gly Asn Phe Leu Glu Pro
            180                 185                 190

Leu Thr Lys Thr Ala Trp Trp Val Pro Val Ala Trp Leu Pro Val
        195                 200                 205

Val Val Tyr His Met Gly Val Ala Leu Lys Asn Met Asn Gln Leu Phe
    210                 215                 220

Ala Cys Phe Leu Phe Cys Val Gly Val Phe Val Trp Thr Leu Ile Glu
225                 230                 235                 240

Tyr Gly Leu His Arg Phe Leu Phe His Phe Asp Asp Trp Leu Pro Glu
                245                 250                 255

Ser Asn Ile Ala Phe Ala Thr His Phe Leu Leu His Gly Cys His His
            260                 265                 270

Tyr Leu Pro Met Asp Lys Tyr Arg Leu Val Met Pro Pro Thr Leu Phe
```

```
                 275                 280                 285
Val Ile Leu Cys Ala Pro Phe Tyr Lys Leu Val Phe Ala Leu Leu Pro
    290                 295                 300

Leu Tyr Trp Ala Tyr Ala Gly Phe Ala Gly Leu Phe Gly Tyr Val
305                 310                 315                 320

Cys Tyr Asp Glu Cys His Phe Phe Leu His His Ser Lys Leu Pro Pro
                325                 330                 335

Phe Met Arg Lys Leu Lys Lys Tyr His Leu Glu His His Tyr Lys Asn
            340                 345                 350

Tyr Gln Leu Gly Phe Gly Val Thr Ser Trp Phe Trp Asp Glu Val Phe
        355                 360                 365

Gly Thr Tyr Leu Gly Pro Asp Ala Pro Leu Ser Lys Met Lys Tyr Glu
    370                 375                 380

<210> SEQ ID NO 9
<211> LENGTH: 1875
<212> TYPE: DNA
<213> ORGANISM: Saccharomyces cerevisiae

<400> SEQUENCE: 9
atggtggtgc agaaaaaact tagggctatc ttgaccgatg aaggtgtatt gatcaaatcg      60
caatcacacc atatgttcaa taagcatggt caactcagaa gcggagattc tttatccttg     120
ttgagctgct tgtcctgtct ggatgatgga actttgagct ctgatggagg ttcttttgat     180
gaggatgatt ccctggaact gttgcctctt aatactacca ttccgttcaa cagaattttg     240
aacgcaaaat atgtgaatgt cggtcagaaa ggcttcaata tggcaaaat ttcttcgaat      300 cctttcaaa cggaaaatct gagttcttcg tctgaaaatg acgacgttga gaatcatagt      360
ttgagcaatg ataaggctcc tgtaagcgaa tcacagtcat ttcccaaaaa agacaagtgg     420
gatacaaaaa cgaacactgt gaaggtgtct cccgatgatt cacaggataa ctcaccatct     480
ttagggataa aagataatca acagttaatt gagttaactt ttgctgtacc caagggccat     540
gatgttatac cacaaaaatt aaccttgtta atagatcacg tttctaggaa atcgagagca     600
aataccggag aggagaacat ttcttctggt actgtggaag aaatcctgga aaaagttat      660 gaaaattcca agagaaacag atcgatatta gtcattatta tccccacgg tggtaaggt      720 actgctaaaa atttattcct gacaaaagca aggccaatac tagtggaaag tggctgcaaa     780
atagaaattg catacacaaa atatgcccgt cacgccatcg atattgccaa agatttagat     840
atcagcaaat acgataccat tgcatgtgcc tcgggtgatg gtattccata cgaagtaatt     900
aatgggcttt atagaagacc cgacagagtg gatgcgttca taaactagc cgtaactcag     960 ctaccttgcg gttcaggaaa tgctatgagc atttcatgtc attggacaaa taccccatcg    1020
tacgccgctc tgtgccttgt caaatccatt gaaacaagaa tagacttaat gtgttgttcc    1080
caaccttctt atatgaacga atggccaaga ttatcctttt tgagtcagac gtacggcgtt    1140
attgcagaat ctgatattaa cactgaattc atcagatgga tgggtcccgt taggtttaat    1200
ttgggtgtag cattcaacat tatccaaggt aagaaatatc cctgcgaagt tttcgtcaaa    1260
tatgctgcca atctaaaaa ggaattaaaa gttcatttct tagaaaataa agataaaaac     1320
aaaggatgtt taaccttcga accaaatcct agcccaaact cttcgccgga tttactatct    1380
aaaaacaata tcaacaacag tacaaaagat gaactttcac cgaattttct caacgaggac    1440
aactttaaat taagtatcc gatgacggaa ccagtaccta gagactggga gaaaatggat     1500
tcagagctaa ctgataactt aacaatcttt tacacaggga aaatgccgta tattgctaag    1560
```

```
gacaccaaat tttttcccgc tgctttacca gcggatggta ccattgattt agtcataacg    1620
gatgcaagaa tcccagtgac aagaatgaca ccaattttat tatccttgga taaaggttct    1680
catgtattag agccagaagt tattcactca aaaatattgg cttataagat tataccaaaa    1740
gtggagtcag gttatttttc agtggatggt gaaaagtttc ctttggaacc cttgcaagtg    1800
gaaataatgc ccatgttatg caagacgttg ctaaggaatg gtagatatat cgatacagag    1860
tttgaatcca tgtag                                                      1875

<210> SEQ ID NO 10
<211> LENGTH: 624
<212> TYPE: PRT
<213> ORGANISM: Saccharomyces cerevisiae

<400> SEQUENCE: 10

Met Val Val Gln Lys Lys Leu Arg Ala Ile Leu Thr Asp Glu Gly Val
1               5                   10                  15

Leu Ile Lys Ser Gln Ser His Met Phe Asn Lys His Gly Gln Leu
            20                  25                  30

Arg Ser Gly Asp Ser Leu Ser Leu Ser Cys Leu Ser Cys Leu Asp
        35                  40                  45

Asp Gly Thr Leu Ser Ser Asp Gly Gly Ser Phe Asp Glu Asp Ser
    50                  55                  60

Leu Glu Leu Leu Pro Leu Asn Thr Thr Ile Pro Phe Asn Arg Ile Leu
65                  70                  75                  80

Asn Ala Lys Tyr Val Asn Val Gly Gln Lys Gly Phe Asn Asn Gly Lys
                85                  90                  95

Ile Ser Ser Asn Pro Phe Gln Thr Glu Asn Leu Ser Ser Ser Glu
            100                 105                 110

Asn Asp Asp Val Glu Asn His Ser Leu Ser Asn Asp Lys Ala Pro Val
        115                 120                 125

Ser Glu Ser Gln Ser Phe Pro Lys Lys Asp Lys Trp Asp Thr Lys Thr
    130                 135                 140

Asn Thr Val Lys Val Ser Pro Asp Asp Ser Gln Asp Asn Ser Pro Ser
145                 150                 155                 160

Leu Gly Ile Lys Asp Asn Gln Gln Leu Ile Glu Leu Thr Phe Ala Val
                165                 170                 175

Pro Lys Gly His Asp Val Ile Pro Gln Lys Leu Thr Leu Leu Ile Asp
            180                 185                 190

His Val Ser Arg Lys Ser Arg Ala Asn Thr Gly Glu Glu Asn Ile Ser
        195                 200                 205

Ser Gly Thr Val Glu Glu Ile Leu Glu Lys Ser Tyr Glu Asn Ser Lys
    210                 215                 220

Arg Asn Arg Ser Ile Leu Val Ile Ile Asn Pro His Gly Gly Lys Gly
225                 230                 235                 240

Thr Ala Lys Asn Leu Phe Leu Thr Lys Ala Arg Pro Ile Leu Val Glu
                245                 250                 255

Ser Gly Cys Lys Ile Glu Ile Ala Tyr Thr Lys Tyr Ala Arg His Ala
            260                 265                 270

Ile Asp Ile Ala Lys Asp Leu Asp Ile Ser Lys Tyr Asp Thr Ile Ala
        275                 280                 285

Cys Ala Ser Gly Asp Gly Ile Pro Tyr Glu Val Ile Asn Gly Leu Tyr
    290                 295                 300

Arg Arg Pro Asp Arg Val Asp Ala Phe Asn Lys Leu Ala Val Thr Gln
305                 310                 315                 320
```

```
Leu Pro Cys Gly Ser Gly Asn Ala Met Ser Ile Ser Cys His Trp Thr
                325                 330                 335

Asn Asn Pro Ser Tyr Ala Ala Leu Cys Leu Val Lys Ser Ile Glu Thr
            340                 345                 350

Arg Ile Asp Leu Met Cys Cys Ser Gln Pro Ser Tyr Met Asn Glu Trp
        355                 360                 365

Pro Arg Leu Ser Phe Leu Ser Gln Thr Tyr Gly Val Ile Ala Glu Ser
    370                 375                 380

Asp Ile Asn Thr Glu Phe Ile Arg Trp Met Gly Pro Val Arg Phe Asn
385                 390                 395                 400

Leu Gly Val Ala Phe Asn Ile Ile Gln Gly Lys Lys Tyr Pro Cys Glu
                405                 410                 415

Val Phe Val Lys Tyr Ala Ala Lys Ser Lys Lys Glu Leu Lys Val His
            420                 425                 430

Phe Leu Glu Asn Lys Asp Lys Asn Lys Gly Cys Leu Thr Phe Glu Pro
        435                 440                 445

Asn Pro Ser Pro Asn Ser Ser Pro Asp Leu Leu Ser Lys Asn Asn Ile
    450                 455                 460

Asn Asn Ser Thr Lys Asp Glu Leu Ser Pro Asn Phe Leu Asn Glu Asp
465                 470                 475                 480

Asn Phe Lys Leu Lys Tyr Pro Met Thr Glu Pro Val Pro Arg Asp Trp
                485                 490                 495

Glu Lys Met Asp Ser Glu Leu Thr Asp Asn Leu Thr Ile Phe Tyr Thr
            500                 505                 510

Gly Lys Met Pro Tyr Ile Ala Lys Asp Thr Lys Phe Phe Pro Ala Ala
        515                 520                 525

Leu Pro Ala Asp Gly Thr Ile Asp Leu Val Ile Thr Asp Ala Arg Ile
    530                 535                 540

Pro Val Thr Arg Met Thr Pro Ile Leu Leu Ser Leu Asp Lys Gly Ser
545                 550                 555                 560

His Val Leu Glu Pro Glu Val Ile His Ser Lys Ile Leu Ala Tyr Lys
                565                 570                 575

Ile Ile Pro Lys Val Glu Ser Gly Leu Phe Ser Val Asp Gly Glu Lys
            580                 585                 590

Phe Pro Leu Glu Pro Leu Gln Val Glu Ile Met Pro Met Leu Cys Lys
        595                 600                 605

Thr Leu Leu Arg Asn Gly Arg Tyr Ile Asp Thr Glu Phe Glu Ser Met
    610                 615                 620

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccttctctag aggatccatg gggagccgcg tctcgcggga agac          44

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
ccttcgaatt ccccgggcca ggggagcttc tgagcatcac tggtc        45

<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctccggcttc tgcggttttt cttagtcttt ccgcaccaat tttcacagga attcccgggg    60
atccgg                                                              66

<210> SEQ ID NO 14
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggataataaa tacaaacgtg ggaagtcgga gacattgcct ttacccagca agctagcttg    60
gctgcagg                                                            68

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctccggcttc tgcggttttt cttagtcttt c                                  31

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggaagtcgga gacattgcct ttacccag                                      28

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgaattcagc cgaaaacagt cttgctt                                       27

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctccatgtcg cttaccaccg cttttagtgc                                30

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgctatactg cagcctcgtc caaaattgtc a                              31

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgaattcttg ccaacctgat ctgtgaa                                   27

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcgctgcata catagacata tacac                                     25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atacgcgatc gctgttaaaa ggaca                                     25

<210> SEQ ID NO 23
<211> LENGTH: 1732
<212> TYPE: DNA
<213> ORGANISM: Homo sapiens

<400> SEQUENCE: 23
gccgccgccg ccgccgccac ctctgagcag ccggctggga gcgagagccg acagctagtc     60
tgcaagccac cgctgtcgcc atggggagcc gcgtctcgcg ggaagacttc gagtgggtct    120
acaccgacca gccgcacgcc gaccggcgcc gggagatcct ggcaaagtat ccagagataa    180
agtccttgat gaaacctgat cccaatttga tatggattat aattatgatg gttctcaccc    240
agttgggtgc attttacata gtaaaagact tggactgaa atgggtcata tttggggcct    300
atgcgtttgg cagttgcatt aaccactcaa tgactctggc tattcatgag attgcccaca    360
atgctgcctt tggcaactgc aaagcaatgt ggaatcgctg gttggaatg tttgctaatc    420 ttcctattgg gattccatat tcaatttcct ttaagaggta tcacatggat catcatcggt    480

```
accttggagc tgatggcgtc gatgtagata ttcctaccga ttttgagggc tggttcttct    540
gtaccgcttt cagaaagttt atatgggtta ttcttcagcc tctctttat gcctttcgac     600 ctctgttcat caaccccaaa ccaattacgt atctggaagt tatcaatacc gtggcacagg    660
tcacttttga cattttaatt tattactttt tgggaattaa atccttagtc tacatgttgg    720
cagcatcttt acttggcctg ggtttgcacc caatttctgg acattttata gctgagcatt    780
acatgttctt aaagggtcat gaaacttact catattatgg gcctctgaat ttacttacct    840
tcaatgtggg ttatcataat gaacatcatg atttccccaa cattcctgga aaaagtcttc    900
cactggtgag gaaaatagca gctgaatact atgacaacct ccctcactac aattcctgga    960
taaaagtact gtatgatttt gtgatggatg atacaataag tccctactca agaatgaaga   1020
ggcaccaaaa aggagagatg gtgctggagt aaatatcatt agtgccaaag ggattcttct   1080
ccaaaacttt agatgataaa atggaatttt tgcattatta aacttgagac cagtgatgct   1140
cagaagctcc cctggcacaa tttcagagta agagctcggt gataccaaga agtgaatctg   1200
gcttttaaac agtcagcctg actctgtact gctcagtttc actcacagga aacttgtgac   1260
ttgtgtatta tcgtcattga ggatgtttca ctcatgtctg tcattttata agcatatcat   1320
ttaaaaagct tctaaaaagc tatttcgcca ggcacggtgg ctcatgccta taatcccagc   1380
actttgggag gccaaggtgg gtggatcacc tgaggtcagg agttcgagac cagcctggcc   1440
aacacggtga accccatctc tactaaaaa tgcaaaaatt agccgggcgt ggcggcacat    1500
gcctgtaatc ccagctacat gggaggctga ggtgggagaa ttgcttgaac ccaggaggcg   1560
gaggcagagg ctgcagtgac ccaagattgt gccactgcac tccaccctgg gcaacagagc   1620
aagaccccat ctcaaaaata aataaatata tataaaaat aaaagctat ttctagttta     1680 tttcactata aagttttgct ttattaaaaa gctaataaac agctattaat cc            1732

<210> SEQ ID NO 24
<211> LENGTH: 2400
<212> TYPE: DNA
<213> ORGANISM: Saccharomyces cerevisiae

<400> SEQUENCE: 24
gaagcaaaaa gatgatttaa cggaagaaag gcatacaaga aggtgaaaat tcgtgtttaa     60
cccatctgat actttccctt gtctaacgta ctgatcctgg aggttatcaa gaacacaaaa    120
gtctagcagc gaaaagtacg cgaagaatct actatagata atggtggtgc agaaaaaact    180
tagggctatc ttgaccgatg aaggtgtatt gatcaaatcg caatcacacc atatgttcaa    240
taagcatggt caactcagaa gcggagattc tttatccttg ttgagctgct tgtcctgtct    300
ggatgatgga actttgagct ctgatggagg ttcttttgat gaggatgatt ccctggaact    360
gttgcctctt aatactacca ttccgttcaa cagaattttg aacgcaaaat atgtgaatgt    420
cggtcagaaa ggcttcaata tggcaaaat ttcttcgaat cctttttcaaa cggaaaatct    480 gagttcttcg tctgaaaatg acgacgttga gaatcatagt ttgagcaatg ataaggctcc    540
tgtaagcgaa tcacagtcat ttcccaaaaa agacaagtgg gatacaaaaa cgaacactgt    600
gaaggtgtct cccgatgatt cacaggataa ctcaccatct ttagggataa aagataatca    660
acagttaatt gagttaactt tgctgtgtacc caagggccat gatgttatac cacaaaaatt    720
aaccttgtta atagatcacg tttctaggaa atcgagagca aataccggag aggagaacat    780
ttcttctggt actgtggaag aaatcctgga aaaaagttat gaaaattcca agagaaacag    840
atcgatatta gtcattatta atccccacgg tggtaaaggt actgctaaaa atttattcct    900
```

```
gacaaaagca aggccaatac tagtggaaag tggctgcaaa atagaaattg catacacaaa    960
atatgcccgt cacgccatcg atattgccaa agatttagat atcagcaaat acgataccat   1020
tgcatgtgcc tcgggtgatg gtattccata cgaagtaatt aatgggcttt atagaagacc   1080
cgacagagtg gatgcgttca ataaactagc cgtaactcag ctaccttgcg gttcaggaaa   1140
tgctatgagc atttcatgtc attggacaaa taacccatcg tacgccgctc tgtgccttgt   1200
caaatccatt gaaacaagaa tagacttaat gtgttgttcc caaccttctt atatgaacga   1260
atggccaaga ttatcctttt tgagtcagac gtacggcgtt attgcagaat ctgatattaa   1320
cactgaattc atcagatgga tgggtcccgt taggtttaat ttgggtgtag cattcaacat   1380
tatccaaggt aagaaatatc cctgcgaagt tttcgtcaaa tatgctgcca aatctaaaaa   1440
ggaattaaaa gttcatttct tagaaaataa agataaaaac aaaggatgtt taaccttcga   1500
accaaatcct agcccaaact cttcgccgga tttactatct aaaaacaata tcaacaacag   1560
tacaaaagat gaactttcac cgaattttct caacgaggac aactttaaat taaagtatcc   1620
gatgacggaa ccagtaccta gagactggga gaaaatggat tcagagctaa ctgataactt   1680
aacaatcttt tacacaggga aaatgccgta tattgctaag gacaccaaat ttttccccgc   1740
tgctttacca gcggatggta ccattgattt agtcataacg gatgcaagaa tcccagtgac   1800
aagaatgaca ccaattttat tatccttgga taaaggttct catgtattag agccagaagt   1860
tattcactca aaaatattgg cttataagat tataccaaaa gtggagtcag gtttattttc   1920
agtggatggt gaaaagtttc cttttggaacc cttgcaagtg gaaataatgc ccatgttatg   1980
caagacgttg ctaaggaatg gtagatatat cgatacagag tttgaatcca tgtagattaa   2040
cgttatattt tccttcaaaa atgatttttt tgtaaaagaa aatactacat cgaaaagaaa   2100
aggcgatata atgtttctat catcggagta tggtttatat tccattttg ttttcattat   2160 aattatacat ccccagttat atatcattaa tacgtaacaa tattatgagt tggtctttat   2220
tatctaatat aattaaaaaa tttacactat tacatcattt tcaaccaata ggatatatat   2280
ataaatatat acatatatgc acattaaatc attcacttgg aagttgcgtc cttcaagcta   2340
actattctat tcaaaataac cttagaagtc gtactctctt tatccagagt gaaataacct   2400
```

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aggttatcaa gaacacaaaa gtctagcagc gaaaagtacg gaattcccgg ggatccg    57

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaggacgcaa cttccaagtg aatgatttaa tgtgcatata tgaagctagc ttggctgcag    60

<210> SEQ ID NO 27
<211> LENGTH: 31

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaagaaaggc atacaagaag gtgaaaattc g                                    31

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctggataaa gagagtacga cttctaagg                                       29

<210> SEQ ID NO 29
<211> LENGTH: 5160
<212> TYPE: DNA
<213> ORGANISM: Saccharomyces cerevisiae

<400> SEQUENCE: 29
aaaaaattcc ggcggttttt cgcgtgtgac tcaatgtcga aatacctgcc taatgaacat      60
gaacatcgcc caaatgtatt tgaagacccg ctgggagaag ttcaagatat ataagtaaca     120
agcagccaat agtataaaaa aaatctgag tttattacct ttcctggaat ttcagtgaaa      180
aactgctaat tatagagaga tatcacagag ttactcacta atgactaacg aaaaggtctg    240
gatagagaag ttggataatc caactctttc agtgttacca catgacttt tacgcccaca     300 acaagaacct tatcgaaac aagctacata ttcgttacag ctacctcagc tcgatgtgcc     360
tcatgatagt ttttctaaca aatacgctgt cgctttgagt gtatgggctg cattgatata    420
tagagtaacc ggtgacgatg atattgttct ttatattgcg aataacaaaa tcttaagatt    480
caatattcaa ccaacgtggt catttaatga gctgtattct acaattaaca atgagttgaa    540
caagctcaat tctattgagg ccaatttttc ctttgacgag ctagctgaaa aaattcaaag    600
ttgccaagat ctggaaagga cccctcagtt gttccgtttg gccttttgg aaaaccaaga     660 tttcaaatta gacgagttca agcatcattt agtggacttt gctttgaatt tggataccag    720
taataatgcg catgttttga acttaattta taacagctta ctgtattcga atgaaagagt    780
aaccattgtt gcggaccaat ttactcaata tttgactgct gcgctaagcg atccatccaa    840
ttgcataact aaaatctctc tgatcaccgc atcatccaag gatagtttac ctgatccaac    900
taagaacttg ggctggtgcg atttcgtggg gtgtattcac gacatttttcc aggacaatgc   960 tgaagccttc ccagagagaa cctgtgttgt ggagactcca acactaaatt ccgacaagtc   1020
ccgttctttc acttatcgcg acatcaaccg cacttctaac atagttgccc attatttgat   1080
taaaacaggt atcaaagag gtgatgtagt gatgatctat tcttctaggg gtgtggattt    1140
gatggtatgt gtgatgggtg tcttgaaagc cggcgcaacc ttttcagtta cgaccctgc    1200 atatcccccca gccagacaaa ccatttactt aggtgttgct aaaccacgtg ggttgattgt    1260
tattagagct gctggacaat tggatcaact agtagaagat tacatcaatg atgaattgga    1320
gattgtttca agaatcaatt ccatcgctat tcaagaaaat ggtaccattg aaggtggcaa    1380
attggacaat ggcgaggatg ttttggctcc atatgatcac tacaaagaca ccagaacagg   1440
tgttgtagtt ggaccagatt ccaacccaac cctatctttc acatctggtt ccgaaggtat   1500
```

```
tcctaagggt gttcttggta gacattttc cttggcttat tatttcaatt ggatgtccaa    1560
aaggttcaac ttaacagaaa atgataaatt cacaatgctg agcggtattg cacatgatcc    1620
aattcaaaga gatatgttta caccattatt tttaggtgcc caattgtatg tccctactca    1680
agatgatatt ggtacaccgg gccgtttagc ggaatggatg agtaagtatg gttgcacagt    1740
tacccattta acacctgcca tgggtcaatt acttactgcc caagctacta caccattccc    1800
taagttacat catgcgttct tgtgggtga cattttaaca aaacgtgatt gtctgaggtt    1860
acaaaccttg gcagaaaatt gccgtattgt taatatgtac ggtaccactg aaacacagcg    1920
tgcagtttct tatttcgaag ttaaatcaaa aaatgacgat ccaaactttt tgaaaaaatt    1980
gaaagatgtc atgcctgctg gtaaaggtat gttgaacgtt cagctactag ttgttaacag    2040
gaacgatcgt actcaaatat gtggtattgg cgaaataggt gagatttatg ttcgtgcagg    2100
tggtttggcc gaaggttata gaggattacc agaattgaat aaagaaaaat ttgtgaacaa    2160
ctggtttgtt gaaaaagatc actggaatta tttggataag gataatggtg aaccttggag    2220
acaattctgg ttaggtccaa gagatagatt gtacagaacg ggtgatttag gtcgttatct    2280
accaaacggt gactgtgaat gttgcggtag ggctgatgat caagttaaaa ttcgtgggtt    2340
cagaatcgaa ttaggagaaa tagatacgca catttcccaa catccattgg taagagaaaa    2400
cattacttta gttcgcaaaa atgccgacaa tgagccaaca ttgatcacat ttatggtccc    2460
aagatttgac aagccagatg acttgtctaa gttccaaagt gatgttccaa aggaggttga    2520
aactgaccct atagttaagg gcttaatcgg ttaccatctt ttatccaagg acatcaggac    2580
tttcttaaag aaaagattgg ctagctatgc tatgccttcc ttgattgtgg ttatggataa    2640
actaccattg aatccaaatg gtaaagttga taagcctaaa cttcaattcc caactcccaa    2700
gcaattaaat ttggtagctg aaaatacagt ttctgaaact gacgactctc agtttaccaa    2760
tgttgagcgc gaggttagag acttatggtt aagtatatta cctaccaagc cagcatctgt    2820
atcaccagat gattcgtttt tcgatttagg tggtcattct atcttggcta ccaaaatgat    2880
ttttacctta aagaaaaagc tgcaagttga tttaccattg gcacaatttt caagtatcc    2940 aacgataaag gcctttgccg cggaaattga cagaattaaa tcatcgggtg gatcatctca    3000
aggtgaggtc gtcgaaaatg tcactgcaaa ttatgcggaa gacgccaaga aattggttga    3060
gacgctacca agttcgtacc cctctcgaga atattttgtt gaacctaata gtgccgaagg    3120
aaaaacaaca attaatgtgt tgttaccgg tgtcacagga tttctgggct cctacatcct    3180
tgcagatttg ttaggacgtt ctccaaagaa ctacagtttc aaagtgtttg cccacgtcag    3240
ggccaaggat gaagaagctg catttgcaag attacaaaag gcaggtatca cctatggtac    3300
ttggaacgaa aaatttgcct caaatattaa agttgtatta ggcgatttat ctaaaagcca    3360
atttggtctt tcagatgaga agtggatgga tttggcaaac acagttgata taattatcca    3420
taatggtgcg ttagttcact gggtttatcc atatgccaaa ttgagggatc caaatgttat    3480
ttcaactatc aatgttatga gcttagccgc cgtcggcaag ccaaagttct ttgactttgt    3540
ttcctccact tctactcttg acactgaata ctactttaat ttgtcagata aacttgttag    3600
cgaagggaag ccaggcattt tagaatcaga cgatttaatg aactctgcaa gcgggctcac    3660
tggtggatat ggtcagtcca atgggctgct gagtacatc attagacgtg caggtgaaag    3720
gggcctacgt gggtgtattg tcagaccagg ttacgtaaca ggtgcctctg ccaatggttc    3780
ttcaaacaca gatgatttct tattgagatt tttgaaggt tcagtccaat taggtaagat    3840
tccagatatc gaaaattccg tgaatatggt tccagtagat catgttgctc gtgttgttgt    3900
```

```
tgctacgtct ttgaatcctc ccaaagaaaa tgaattggcc gttgctcaag taacgggtca    3960
cccaagaata ttattcaaag actacttgta tactttacac gattatggtt acgatgtcga    4020
aatcgaaagc tattctaaat ggaagaaatc attggaggcg tctgttattg acaggaatga    4080
agaaaatgcg ttgtatcctt tgctacacat ggtcttagac aacttacctg aaagtaccaa    4140
agctccggaa ctagacgata ggaacgccgt ggcatcttta aagaaagaca ccgcatggac    4200
aggtgttgat tggtctaatg gaataggtgt tactccagaa gaggttggta tatatattgc    4260 attttaaac aaggttggat ttttacctcc accaactcat aatgacaaac ttccactgcc    4320
aagtatagaa ctaactcaag cgcaaataag tctagttgct tcaggtgctg gtgctcgtgg    4380
aagctccgca gcagcttaag gttgagcatt acgtatgata tgtccatgta caataattaa    4440
atatgaatta ggagaaagac ttagcttctt ttcgggtgat gtcacttaaa aactccgaga    4500
ataatatata ataagagaat aaaatattag ttattgaata agaactgtaa atcagctggc    4560
gttagtctgc taatggcagc ttcatcttgg tttattgtag catgaatcat atttgccttt    4620
ttttcctgta attcaatgat tcttgcttct atactatcct caatgcaaaa ccttgtgatc    4680
ttcacaggtc gatactgacc aattctatga actctatcac cactttgcca ttcaacacta    4740
gggttccacc atgggtctaa aatgaatact tgcgaagctt cacaaagatt caaagcaaca    4800
ccgcccgcct ttaaactgac caagaaaacc tcgcattgaa tgttgttcat gaaatacttg    4860
atggtttcat ctctttgcgt cggtgacata ctaccctgaa gcttcactgt ttgaaatcca    4920
gctcttttca atctccactc taccagatcc agcatactgg taaactggga aaacacaatg    4980
gatttaatcg ttctcttgtt gcttctcagt ttgtatagtt cttccacaag tgcttcgatt    5040
ttcgttgatg attgccactt gccactcatg tttagacggc taacaatact ttgcttttttg   5100 aaggaatcaa ggtccacttc caaagcaggt tgagacaaat cgatacttag cccgatatga    5160

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
actgcagaat tccggcggtt tttcgcgtg                                       29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acccggggat tgtctcaac ctgctttgg                                        29
```

METHODS FOR PRODUCING HUMAN CERAMIDE USING YEAST TRANSFORMANTS

CROSS REFERENCE TO RELATED APPLICATIONS

This application is the National Stage of International Application No. PCT/JP2008/059241, filed May 20, 2008, and claims benefit of Japanese Application No. 2007-149657, filed Jun. 5, 2007, which are incorporated herein in their entirety.

REFERENCE TO A SEQUENCE LISTING

A sequence listing comprising SEQ ID NOS: 1-31 are incorporated herein by reference.

TECHNICAL FIELD

The present application claims priority based on Japanese Patent Application No. 2007-149657 filed on Jun. 5, 2007.

The present invention relates to methods for producing human ceramide in cells such as yeast cells.

BACKGROUND ART

A tissue known as stratum corneum exists on the outermost layer of the skin, which has a moisturizing function for retaining moisture as well as a barrier function for protecting the skin against external stimulation. The stratum corneum consists of keratinocytes, natural moisturizing factors and intercellular lipids, among which ceramides account for approximately one-half of the total intercellular lipids and play a crucial role for these functions. For example, a common characteristic of atopic dermatitis and senile xerosis is a significant deterioration of moisturizing ability, which is known to mainly result from decreased ceramide levels due to lipid metabolic enzyme abnormalities. Ceramides have also been shown to enhance barrier function, provide whitening effect and inhibit melanogenesis. Ceramides can be externally supplied.

J Invest Dermatol. 96:523-526, 1991 (Non-patent document 1) and Arch Dermatol Res. 283:219-223, 1991 (Non-patent document 2) disclose "decreased ceramide levels in atopic dermatitis and senile xerosis"; J Dermatol Sci. 1:79-83, 1990 (Non-patent document 3) and Acta Derm Venereol. 74:337-340, 1994 (Non-patent document 4) disclose "decreased ceramide levels and lipid metabolic enzyme abnormalities"; Contact Dermatitis. 45:280-285, 2001 (Non-patent document 5) and J Eur Acad Dermatol Venereol. 16:587-594, 2002 (Non-patent document 6) disclose "restoration of barrier function by ceramides"; and Cell Signal 14:779-785, 2002 (Non-patent document 7) discloses "inhibition of melanogenesis by ceramides."

Recently, ceramides have attracted great attention for use in medicines for skin diseases associated with dry sensitive skin or in cosmetics or health and/or cosmeceutical foods. In fact, a number of products such as cosmetics and food or supplements containing ceramides have already been commercialized, and the market for ceramide materials is continuing to grow.

Ceramide materials of animal origin such as cow were conventionally used, but are currently replaced by those of plant origin such as rice, wheat, soybean and potato because of problems of infections. A recent basic study (J. Clin. Invest. 112:1372-1382, 2003 (Non-patent document 8)) showed the importance of the structures of ceramides in the moisturizing and barrier functions of the skin, which raised questions about whether plant ceramides structurally different from human ceramides are highly functional lipids. Moreover, ceramides are present in animals and plants in minute amounts and are difficult to extract and purify, thus incurring low productivity and high cost, and therefore, it is highly desirable to develop a new production technique capable of overcoming these problems.

It is known that, in the synthetic/metabolic pathway for sphingolipids, reactions downstream of dihydrosphingosine (DHS) biosynthesis widely differ between higher animal cells (including human cells) and yeast cells, as shown in FIG. 1. Each enzyme protein involved in various steps in the synthetic/metabolic pathway for sphingolipids and the gene encoding the protein have been known to some degree (Biochemistry. 41:15105-15114, 2002 (Non-patent document 9); J Biol Chem. 277:25512-25518, 2002 (Non-patent document 10); Yeast 9: 267-277, 1993 (Non-patent document 11); J Biol Chem 272:29704-29710, 1997 (Non-patent document 12); J Biol Chem 275:31369-31378, 2000 (Non-patent document 13); J Biol Chem 275:39793-39798, 2000 (Non-patent document 14)).

Non-patent document 1: J Invest Dermatol. 96:523-526, 1991
Non-patent document 2: Arch Dermatol Res. 283:219-223, 1991
Non-patent document 3: J Dermatol Sci. 1:79-83, 1990
Non-patent document 4: Acta Derm Venereol. 74:337-340, 1994
Non-patent document 5: Contact Dermatitis. 45:280-285, 2001
Non-patent document 6: J Eur Acad Dermatol Venereol. 16:587-594, 2002
Non-patent document 7: Cell Signal 14:779-785, 2002
Non-patent document 8: J. Clin. Invest. 112:1372-1382, 2003
Non-patent document 9: Biochemistry. 41:15105-15114, 2002
Non-patent document 10: J Biol Chem. 277:25512-25518, 2002
Non-patent document 11: Yeast 9: 267-277, 1993
Non-patent document 12: J Biol Chem 272:29704-29710, 1997
Non-patent document 13: J Biol Chem 275:31369-31378, 2000
Non-patent document 14: J Biol Chem 275:39793-39798, 2000

DISCLOSURE OF THE INVENTION

Problems to be Solved by the Invention

Plant ceramides structurally differ from human ceramide, and their productivity is low. To overcome these problems, it is highly desirable to develop a new production technique capable of producing human ceramide by using cells such as yeast cells.

Means for Solving the Problems

As a result of careful studies to solve the problems described above, the inventors of the present invention have achieved the present invention.

The present invention aims to develop a system for efficient production of highly functional human ceramide by gene recombination technology and successful control of the ceramide synthetic/metabolic and transport systems in eukaryotic organisms. To this end, budding yeast is used as a host because it is relatively easy to handle in gene manipulation and has been traditionally used for food manufacturing.

Specifically, a target of the present invention is ceramide NS, which exists in human stratum corneum with the highest distribution and is deemed crucial for the moisturizing and barrier functions of the skin. The structures of ceramides depend on the types of enzymes possessed by cells, and vary between species. Budding yeast used as a host possesses no enzyme for synthesizing ceramide NS, which is a main ceramide in higher animals. Instead, the host possesses an enzyme for synthesizing its inherent ceramide. Thus, to synthesize ceramide NS in yeast cells, the host-derived ceramide synthetic pathway must be inhibited and necessary enzymes must be introduced into yeast cells.

Specifically, in the synthetic/metabolic pathway for sphingolipids, reactions downstream of dihydrosphingosine (DHS) biosynthesis widely differ between higher animal cells (including human cells) and yeast cells, as shown in FIG. 1. Namely, no human sphingoid base (sphingosine) having a double bond at C-4 of DHS is synthesized in budding yeast (genus *Saccharomyces*) due to the absence of the sphingolipid Δ4-desaturase gene (DES1) (FIG. 2). Instead, phytosphingosine (PHS) is synthesized by hydroxylation of C-4 of DHS by an enzyme encoded by the sphinganine C4-hydroxylase gene (SUR2). Alternatively, DHS is phosphorylated by an enzyme encoded by the sphingoid base kinase gene (LCB4) to synthesize dihydrosphingosine monophosphate.

Once sphingoid bases are synthesized efficiently, it can be expected that they will be converted into ceramides.

First, the inventors of the present invention thought it important for production of human ceramide in yeast cells: 1) to allow yeast cells to express a sphingolipid Δ4-desaturase enzyme not present in yeast cells; 2) to completely or even partially abolish sphinganine C4-hydroxylase enzyme activity; and 3) to completely or even partially abolish sphingoid base kinase enzyme activity. Thus, the inventors initially attempted to prepare a disruption strain of the SUR2 and LCB4 genes, and to introduce the human DES1 gene into the variant strain by transformation of yeast. This enabled the production of human ceramide in yeast cells for the first time, which had not been possible before.

As used herein, human ceramide refers to ceramide NS having the structural formula shown as "target product" in FIG. 2, for example. In contrast, phytoceramide is yeast ceramide, which differs from the human ceramide in that the double bond at the 4-position of the human ceramide is substituted by a hydroxy group (FIG. 3).

The inventors further optimized the method of the present invention to construct a system for efficiently producing human ceramide NS. Specifically, the inventors succeeded in producing human ceramide more efficiently by transformation of yeast with step 4) shown below:

4) abolishing the expression of the yeast sphingolipid α-hydroxylase gene (SCSI) to prevent hydroxylation of ceramide NS.

Thus, the present invention provides methods for conveniently and efficiently producing human ceramide in yeast cells by including 1) to 3) above as essential features, and 4) as an additional feature in preferred embodiments. The present invention preferably encompasses the following embodiments.

Embodiment 1

A method for producing human ceramide in a yeast cell, which comprises:

1) introducing the sphingoid Δ4-desaturase gene (DES1) by transformation of the yeast cell;

2) abolishing the expression of the yeast sphinganine C4-hydroxylase gene (SUR2) by transformation of the yeast cell; and 3) abolishing the expression of the yeast sphingoid base kinase gene (LCB4) by transformation of the yeast cell.

Embodiment 2

The method according to Embodiment 1, wherein the yeast sphingoid base kinase gene (LCB4) encodes a protein having the amino acid sequence of SEQ ID NO: 10 or an amino acid sequence obtained by deletion, addition or substitution of one or more amino acid residues in SEQ ID NO: 10, and having sphingoid base kinase activity.

Embodiment 3

The method according to Embodiment 1 or 2, wherein the sphingoid Δ4-desaturase gene (DES1) encodes a protein having the amino acid sequence of SEQ ID NO: 2 or an amino acid sequence obtained by deletion, addition or substitution of one or more amino acid residues in SEQ ID NO: 2, and having sphingoid Δ4-desaturase activity.

Embodiment 4

The method according to any one of Embodiments 1 to 3, wherein the yeast sphinganine C4-hydroxylase gene (SUR2) encodes a protein having the amino acid sequence of SEQ ID NO: 6 or an amino acid sequence obtained by deletion, addition or substitution of one or more amino acid residues in SEQ ID NO: 6, and having sphinganine C4-hydroxylase activity.

Embodiment 5

The method according to any one of Embodiments 1 to 4, which further comprises 4) abolishing the expression of the yeast sphingolipid α-hydroxylase gene (SCS7) by transformation of the yeast cell.

Embodiment 6

The method according to any one of Embodiments 1 to 5, wherein the yeast sphingolipid α-hydroxylase gene (SCS7) encodes a protein having the amino acid sequence of SEQ ID NO: 8 or an amino acid sequence obtained by deletion, addition or substitution of one or more amino acid residues in SEQ ID NO: 8, and having sphingolipid α-hydroxylase activity.

Embodiment 7

The method according to any one of Embodiments 1 to 6, wherein the yeast is selected from yeast species of the genus *Saccharomyces*.

Embodiment 8

The method according to any one of Embodiments 1 to 7, wherein two or more DES1 expression vectors carrying mutually different selectable markers are used for 1) introduction of the sphingoid Δ4-desaturase gene (DES1).

Sphingolipid Δ4-desaturase Gene (DES1)

As essential feature 1), the methods of the present invention comprise introducing the sphingolipid Δ4-desaturase gene (DES1) by transformation of the yeast cell.

DES1 preferably encodes, but is not limited to, a protein having the amino acid sequence of SEQ ID NO: 2 or an amino acid sequence obtained by deletion, addition or substitution of one or more amino acid residues in SEQ ID NO: 2, and having sphingolipid Δ4-desaturase activity.

Genes (nucleic acids) that can be used in the present invention include genomic DNAs (including their corresponding cDNAs), chemically synthesized DNAs, DNAs amplified by PCR, and combinations thereof.

DES1 preferably has the nucleotide sequence of SEQ ID NO: 1. This is a nucleotide sequence encoding a human sphingolipid Δ4-desaturase protein having the amino acid sequence of SEQ ID NO: 2, and it is disclosed in, for example, GenBanK: accession number AF466375.

One or more codons may encode the same amino acid, and this is called degeneracy of the genetic code. Thus, a DNA sequence not completely identical to SEQ ID NO: 1 may encode a protein having an amino acid sequence completely identical to SEQ ID NO: 2. Such a variant DNA sequence may result from silent mutation (e.g., occurring during PCR amplification), or can be the product of deliberate mutagenesis of a native sequence.

DES1 preferably encodes the amino acid sequence of SEQ ID NO: 2. However, it may also have an amino acid sequence obtained by deletion, addition or substitution of one or more amino acid residues. It is intended to encompass any homologous protein so long as it has sphingolipid Δ4-desaturase activity. The present invention is not limited to SEQ ID NO: 2 in so far as an amino acid sequence having a comparable function to that of SEQ ID NO: 2 is encoded. "Amino acid change" involves one or more amino acids, preferably 1-20, more preferably 1-10, most preferably 1-5 amino acids.

The amino acid sequence encoded by DES1 has an identity of at least about 70%, preferably about 80% or more, more preferably 90% or more, still more preferably 95% or more, and most preferably 98% or more to the amino acid sequence of SEQ ID NO: 2.

The percent amino acid identity may be determined by visual inspection and mathematical calculation. Alternatively, the percent identity of two protein sequences can be determined by comparing sequence information using the GAP computer program, based on the algorithm of Needleman, S. B. and Wunsch, C. D. (J. Mol. Biol., 48: 443-453, 1970), available from the University of Wisconsin Genetics Computer Group (UWGCG). The preferred default parameters for the GAP program include: (1) a scoring matrix, blosum62, as described by Henikoff, S and Henikoff, J. G. (Proc. Natl. Acad. Sci. USA, 89: 10915-10919, 1992); (2) a gap weight of 12; (3) a gap length weight of 4; and (4) no penalty for end gaps.

Other programs used by those skilled in the art of sequence comparison may also be used. The percent identity can be determined by comparing sequence information using the BLAST program described by Altschul et al. (Nucl. Acids. Res. 25, pp. 3389-3402, 1997), for example. This program is available at the website of National Center for Biotechnology Information (NCBI) or DNA Data Bank of Japan (DDBJ) on the Internet. Various conditions (parameters) for homology searches with the BLAST program are described in detail on the site, and searches are normally performed with default values, though some settings may be appropriately changed.

In the methods of the present invention, sphingolipid Δ4-desaturase preferably has the amino acid sequence of SEQ ID NO: 2 or an amino acid sequence at least 70% identical to SEQ ID NO: 2, and has sphingolipid Δ4-desaturase activity.

It is well known to those skilled in the art that even proteins having the same function may have different amino acid sequences depending on the varieties from which they are derived. DES1 may include such homologs and variants of the nucleotide sequence of SEQ ID NO: 1 so long as they have sphingolipid Δ4-desaturase activity. In addition to the human sphingolipid Δ4-desaturase protein of SEQ ID NO: 2, the presence of genes encoding proteins showing a similar activity is known in, for example, mouse (*M. musculus*), drosophila (*D. melanogaster*), nematode (*C. elegans*), fission yeast (*Schizosaccharomyces pombe*), etc. (Non-patent document 10).

The expression "having sphingolipid Δ4-desaturase activity" refers to the activity of introducing a double bond into C-4 of dihydrosphingosine to synthesize sphingosine, as shown in FIG. 2 or FIG. 3. Alternatively, it refers to the activity of introducing a double bond into C-4 of dihydroceramide to synthesize ceramide NS. Introduction of DES1 allows transformant yeast cells to synthesize sphingosine and/or ceramide NS that are not synthesized in the natural metabolic pathway of yeast.

A preferred sphingolipid Δ4-desaturase gene of the present invention also includes a nucleic acid capable of hybridizing to the nucleotide sequence of SEQ ID NO: 1 under stringent conditions, e.g., under conditions of moderate or high stringency and having sphingoid Δ4-desaturase activity.

The expression "under stringent conditions" refers to hybridization under conditions of moderate or high stringency. Specifically, conditions of moderate stringency can be readily determined by those having ordinary skill in the art based on, for example, the length of the DNA. The basic conditions are set forth by Sambrook et al., Molecular Cloning: A Laboratory Manual, 3rd Ed., Chapters 6-7, Cold Spring Harbor Laboratory Press, 2001, and include use of a prewashing solution for the nitrocellulose filters 5×SSC, 0.5% SDS, 1.0 mM EDTA (pH 8.0), hybridization conditions of about 50% formamide, 2×SSC to 6×SSC at about 40° C. to 50° C. (or other similar hybridization solution, such as Stark's solution, in about 50% formamide at about 42° C.), and washing conditions of about 40° C. to 60° C., 0.5 to 6×SSC, 0.1% SDS. Preferably, conditions of moderate stringency include hybridization conditions (and washing conditions) of 6×SSC at about 50° C. Conditions of high stringency can also be readily determined by the skilled artisan based on, for example, the length of the DNA.

Generally, such conditions include hybridization and/or washing at higher temperatures and/or lower salt concentrations than in the conditions of moderate stringency (e.g., hybridization in 6×SSC to 0.2×SSC, preferably 6×SSC, more preferably 2×SSC, most preferably 0.2×SSC at about 65° C.), and are defined to involve hybridization conditions as above and washing in 0.2×SSC, 0.1% SDS at about 65° C. to 68° C. SSPE (1×SSPE=0.15 M NaCl, 10 mM NaH$_2$PO$_4$, and 1.25 mM EDTA, pH 7.4) can be substituted for SSC (1×SSC=0.15 M NaCl and 15 mM sodium citrate) for use as hybridization and washing buffers, and washing is continued for 15 minutes after completion of hybridization.

As known by those skilled in the art and as further described below, it should be understood that the washing temperature and the washing salt concentration can be adjusted as desired to achieve a desirable degree of stringency by applying basic principles governing hybridization reaction and duplex stability (see, e.g., Sambrook et al., 2001). When a nucleic acid is to be hybridized to a target nucleic acid of an unknown sequence, the length of the hybrid is assumed to be that of the nucleic acid to be hybridized. When nucleic acids of known sequences are to be hybridized, the length of the hybrid can be determined by aligning the sequences of the nucleic acids and identifying a single or multiple region(s) having optimal sequence complementarity. The hybridization temperature of a hybrid estimated to have a length of less than 50 bp must be 5-25° C. lower than the melting temperature ($T_m$) of the hybrid, where $T_m$ is determined by the equation below. For hybrids having a length of less than 18 bp, $T_m$ (° C.)=2 (the number of A+T bases)+4 (the number of G+C bases). For hybrids having a length of 18 bp or more, $T_m$=81.5° C.+16.6 ($\log_{10}$[Na$^+$])+41 (mole fraction [G+C])– 0.63 (% formamide)–500/n, where N is the number of bases in the hybrid, and [Na$^+$] is the sodium ion concentration in the hybridization buffer ([Na$^+$] in 1×SSC=0.165 M). Preferably, such hybridizing nucleic acids each have a length of at least 8 nucleotides (or more preferably at least 15 nucleotides, or at least 20 nucleotides, or at least 25 nucleotides, or at least 30 nucleotides, or at least 40 nucleotides, or most preferably at least 50 nucleotides), or a length of at least 1% (more preferably at least 25%, or at least 50%, or at least 70%, and most preferably at least 80%) of the length of a nucleic acid to which it hybridizes, and has a sequence identity of at least 50% (more preferably at least 70%, at least 75%, at least 80%, at least 85%, at least 90%, at least 95%, at least 97.5%, or at least 99%, and most preferably at least 99.5%) to a nucleic acid to which it hybridizes. The sequence identity here is determined by comparing the sequences of the nucleic acids to be hybridized when aligned so as to maximize overlap and identity while minimizing sequence gaps, as described in detail above.

The percent nucleic acid identity can be determined by visual inspection and mathematical calculation. Alternatively, the percent identity of two nucleic acid sequences can be determined by visual inspection and mathematical calculation, or more preferably, the comparison is made by comparing sequence information using a computer program. An exemplary, preferred computer program is the Genetics Computer Group (GCG; Madison, Wis.) Wisconsin package version 10.0 program, "GAP" (Devereux et al., 1984, Nucl. Acids Res. 12: 387). This "GAP" program can be used to compare not only two nucleic acid sequences but also two amino acid sequences or a nucleic acid sequence and an amino acid sequence. The preferred default parameters for the "GAP" program include (1) The GCG implementation of a unary comparison matrix (containing a value of 1 for identities and 0 for non-identities) for nucleotides, and the weighted amino acid comparison matrix of Gribskov and Burgess, Nucl. Acids Res. 14: 6745, 1986 as described by Schwartz and Dayhoff, eds., "Atlas of Polypeptide Sequence and Structure", National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website, or the WU-BLAST 2.0 algorithm. In addition, the BLAST algorithm uses the BLOSUM62 amino acid scoring matix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, Methods Enzymol. 266: 544-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The sphingolipid Δ4-desaturase gene (DES1) of the present invention also includes a nucleic acid having a nucleotide sequence different from that of SEQ ID NO: 1 by deletion, insertion or substitution of one or more nucleotides, but still encoding a protein having sphingolipid Δ4-desaturase activity. The number of nucleotides deleted, inserted or substituted is not limited so long as a protein having sphingolipid Δ4-desaturase activity is encoded, but is preferably 1 to several thousands, more preferably 1 to 1,000, more preferably 1 to 500, still more preferably 1 to 200, most preferably 1 to 100.

A given amino acid may be replaced, for example, by a residue having similar physiochemical characteristics. Examples of such conservative substitutions include changes from one aliphatic residue to another, such as changes from one to another of Ile, Val, Leu, or Ala; changes from one polar residue to another, such as Lys to Arg, Glu to Asp, or Gln to Asn; or changes from one aromatic residue to another, such as changes from one to another of Phe, Trp, or Tyr. Other well-known conservative substitutions include, for example, changes between entire regions having similar hydrophobic characteristics. Those skilled in the art can introduce desired deletions, insertions or substitutions by well-known gene engineering techniques using, for example, site-specific mutagenesis as described in Sambrook et al. (2001), supra.

Yeast Sphinganine C4-hydroxylase Gene (SUR2)

As essential feature 2), the methods of the present invention comprise abolishing the expression of the yeast sphinganine C4-hydroxylase gene (SUR2) by transformation of the yeast cell.

SUR2 preferably encodes, but is not limited to, a protein having the amino acid sequence of SEQ ID NO: 6 or an amino acid sequence obtained by deletion, addition or substitution of one or more amino acid residues in SEQ ID NO: 6, and having sphinganine C4-hydroxylase activity.

SUR2 preferably has the nucleotide sequence of SEQ ID NO: 5. This is a nucleotide sequence encoding a yeast sphinganine C4-hydroxylase protein having the amino acid sequence of SEQ ID NO: 6, and it is disclosed in, for example, SGD (Saccharomyces Genome Database.

SUR2 preferably encodes the amino acid sequence of SEQ ID NO: 6. However, it may also have an amino acid sequence obtained by deletion, addition or substitution of one or more amino acid residues. It is intended to encompass any homologous protein so long as it has sphinganine C4-hydroxylase activity. The present invention is not limited to SEQ ID NO: 6 so long as an amino acid sequence having a comparable function to that of SEQ ID NO: 6 is encoded. "Amino acid change" involves one or more amino acids, preferably 1-20, more preferably 1-10, most preferably 1-5 amino acids.

The expression "having sphinganine C4-hydroxylase activity" refers to the activity of introducing a hydroxyl group into C-4 of dihydrosphingosine to synthesize phytosphingosine, as shown in FIG. 2 or FIG. 3. Alternatively, it refers to the activity of introducing a hydroxyl group into C-4 of dihydroceramide to synthesize phytoceramide. In the present invention, the synthesis of phytosphingosine and/or phytoceramide that are synthesized in the natural metabolic pathway of yeast is partially or completely inhibited by partially or completely abolishing the expression of SUR2 by transformation of the yeast cell. Sphingosine and/or ceramide NS can be efficiently synthesized by suppressing the expression of the SUR2 gene and expressing the DES1 gene.

The amino acid sequence encoded by SUR2 has an identity of at least about 70%, preferably about 80% or more, more preferably 90% or more, still more preferably 95% or more, and most preferably 98% or more to the amino acid sequence of SEQ ID NO: 6.

A preferred yeast sphinganine C4-hydroxylase gene (SUR2) of the present invention also includes a nucleic acid capable of hybridizing to the nucleotide sequence of SEQ ID NO: 5 under stringent conditions, e.g., under conditions of moderate or high stringency and having yeast sphinganine C4-hydroxylase activity.

The yeast sphinganine C4-hydroxylase gene (SUR2) of the present invention also includes a nucleic acid having a nucleotide sequence different from that of SEQ ID NO: 5 by deletion, insertion or substitution of one or more nucleotides, but still encoding a protein having sphinganine C4-hydroxylase activity.

Common matters such as "deletion, addition or substitution of amino acids and/or nucleotides", "percent identity of amino acids and/or nucleotides", hybridization "under stringent conditions" are as described above for DES1.

Sphingoid Base Kinase Gene (LCB4)

As essential feature 3), the methods of the present invention comprise abolishing the expression of the sphingoid base kinase gene (LCB4) by transformation of the yeast cell.

LCB4 encodes a protein having kinase activity on sphingoid bases, as shown in FIGS. 1 and 2, for example. LCB4 activity phosphorylates sphingoid bases to reduce the intracellular levels of sphingoid bases. For more efficient production of human ceramide, it is more effective to disrupt the LCB4 gene to thereby increase the intracellular levels of sphingoid bases. Thus, the present invention comprises abolishing the expression of LCB4.

LCB4 preferably encodes, but is not limited to, a protein having the amino acid sequence of SEQ ID NO: 10 or an amino acid sequence obtained by deletion, addition or substitution of one or more amino acid residues in SEQ ID NO: 10, and having sphingoid base kinase activity.

LCB4 preferably has the nucleotide sequence of SEQ ID NO: 9. This is a nucleotide sequence encoding a yeast sphingoid base kinase protein having the amino acid sequence of SEQ ID NO: 10, and it is disclosed in, for example, SGD (Saccharomyces Genome Database.

LCB4 preferably encodes the amino acid sequence of SEQ ID NO: 10. However, it may also have an amino acid sequence obtained by deletion, addition or substitution of one or more amino acid residues. It is intended to encompass any homologous protein so long as it has sphingoid base kinase activity. The present invention is not limited to SEQ ID NO: 10 so long as an amino acid sequence having a comparable function to that of SEQ ID NO: 10 is encoded. "Amino acid change" involves one or more amino acids, preferably 1-20, more preferably 1-10, most preferably 1-5 amino acids.

The expression "having sphingoid base kinase activity" refers to the activity of phosphorylating dihydrosphingosine to synthesize dihydrosphingosine monophosphate, as shown in FIGS. 1 to 3, for example. In the present invention, undesirable phosphorylation of dihydrosphingosine is inhibited by partially or completely abolishing the expression of LCB4 by transformation of the yeast cell.

The amino acid sequence encoded by LCB4 has an identity of at least about 70%, preferably about 80% or more, more preferably 90% or more, still more preferably 95% or more, and most preferably 98% or more to the amino acid sequence of SEQ ID NO: 10.

A preferred yeast sphingoid base kinase gene (LCB4) of the present invention also includes a nucleic acid capable of hybridizing to the nucleotide sequence of SEQ ID NO: 9 under stringent conditions, e.g., under conditions of moderate or high stringency and having yeast sphingoid base kinase activity.

The yeast sphingoid base kinase gene (LCB4) of the present invention also includes a nucleic acid having a nucleotide sequence different from that of SEQ ID NO: 9 by deletion, insertion or substitution of one or more nucleotides, but still encoding a protein having sphingoid base kinase activity.

Common matters such as "deletion, addition or substitution of amino acids and/or nucleotides", "percent identity of amino acids and/or nucleotides", hybridization "under stringent conditions" are as described above for DES1.

Yeast Sphingolipid α-hydroxylase Gene SCS7)

If desired, as additional feature 4), the methods of the present invention may further comprise abolishing the expression of the yeast sphingolipid α-hydroxylase gene (SCS7) by transformation of the yeast cell. SCS7 has the activity of adding a hydroxyl group to the α-carbon of a fatty acid amide-linked to the sphingoid base of phytoceramide, dihydroceramide, and ceramide NS to synthesize Cer(AP), Cer(ASa), and Cer(AS), respectively, in FIG. 2 or FIG. 3, for example. Even if desired dihydroceramide or ceramide NS is synthesized, it is further hydroxylated by the presence of SCS7 activity. Thus, the present invention preferably comprises abolishing the expression of SCS7.

SCS7 preferably encodes, but is not limited to, a protein having the amino acid sequence of SEQ ID NO: 8 or an amino acid sequence obtained by deletion, addition or substitution of one or more amino acid residues in SEQ ID NO: 8, and having sphingolipid α-hydroxylase activity.

SCS7 preferably has the nucleotide sequence of SEQ ID NO: 7. This is a nucleotide sequence encoding a yeast sphingolipid α-hydroxylase protein having the amino acid sequence of SEQ ID NO: 8, and it is disclosed in, e.g., SGD (Saccharomyces Genome Database.

SCS7 preferably encodes the amino acid sequence of SEQ ID NO: 8. However, it may also have an amino acid sequence obtained by deletion, addition or substitution of one or more amino acid residues. It is intended to encompass any homologous protein so long as it has sphingolipid α-hydroxylase activity. The present invention is not limited to SEQ ID NO: 8 so long as an amino acid sequence having a comparable function to that of SEQ ID NO: 8 is encoded. "Amino acid change" involves one or more amino acids, preferably 1-20, more preferably 1-10, most preferably 1-5 amino acids.

The expression "having sphingolipid α-hydroxylase activity" refers to the activity of adding a hydroxyl group to the α-carbon of a fatty acid amide-linked to the sphingoid base of phytoceramide, dihydroceramide, and ceramide NS to synthesize Cer(AP), Cer(ASa), and Cer(AS), respectively, as shown in FIG. 7, for example. In the present invention, undesirable hydroxylation of dihydroceramide or ceramide NS is inhibited by partially or completely abolishing the expression of SCS7, preferably by transformation of the yeast cell.

The amino acid sequence encoded by SCS7 has an identity of at least about 70%, preferably about 80% or more, more preferably 90% or more, still more preferably 95% or more, and most preferably 98% or more to the amino acid sequence of SEQ ID NO: 8.

A preferred yeast sphingolipid α-hydroxylase gene (SCS7) of the present invention also includes a nucleic acid capable of hybridizing to the nucleotide sequence of SEQ ID NO: 7 under stringent conditions, e.g., under conditions of moderate or high stringency and having yeast sphingolipid α-hydroxylase activity.

The yeast sphingolipid α-hydroxylase gene (SCS7) of the present invention also includes a nucleic acid having a nucleotide sequence different from that of SEQ ID NO: 7 by deletion, insertion or substitution of one or more nucleotides, but still encoding a protein having sphingolipid α-hydroxylase activity.

Common matters such as "deletion, addition or substitution of amino acids and/or nucleotides", "percent identity of amino acids and/or nucleotides", hybridization "under stringent conditions" are as described above for DES1.

Methods for Introducing and Expressing Genes by Transformation of Yeast

In the present invention, the expression of DES1 in the yeast cell can be performed by any known method. Preferably, the method comprises transforming a host yeast cell with an expression vector containing DES1, and cultivating the transformant yeast cell under conditions allowing the expression of the nucleic acid.

The yeast species that can be used in the methods of the present invention are preferably, but are not limited to, yeast species of the genus Saccharomyces. Saccharomyces cerevisiae, Saccharomyces pastorianus, Saccharomyces bayanus, and Saccharomyces kluyveri are more preferred. Budding yeast species including the genus Saccharomyces have been analyzed most extensively for ceramide synthesis and metabolism at the genetic level. Thus, they can be used to rapidly optimize the methods for producing human ceramide according to the present invention. Moreover, yeast cells are easy to culture and have been traditionally used for food manufacturing. In addition, they can be used to establish a method for extracting/purifying large amounts of ceramides conveniently, safely and inexpensively.

In the present invention, known yeast expression vectors can be used to introduce and express genes. In the examples below, known gene expression vectors for yeast pRS series (p4XX) (Mumberg et al., Gene, 156, 119, 1995) and pYE22m (Ashikari et al., Appl Microbiol Biotechnol, 30, 515, 1989) were used.

Any of multicopy (YEp), single copy (YCp), and chromosome integration (YIp) vectors can be used for introduction into yeast. For example, a number of expression vectors for yeast are known to those skilled in the art and can be used in the methods of the present invention, including YEp vectors such as YEp24 (J. R. Broach et al., Experimental Manipulation of Gene Expression, Academic Press, New York, 83, 1983), YCp vectors such as YCp50 (M. D. Rose et al., gene, 60, 237, 1987), and YIp vectors such as YIp5 (K. Struhl et al., Proc. Natl. Acad. Sci. USA, 76, 1035, 1979).

In addition to each gene of interest, expression vectors can typically contain a selectable marker and an origin of replication for proliferation in host cells. Vectors also optionally contain a transcription or translation regulatory sequence preferably derived from yeast fused to a nucleic acid of the present invention.

Examples of regulatory sequences include transcriptional promoters, operators, or enhancers, an mRNA ribosomal binding site, and appropriate sequences which control the initiation and termination of transcription and translation. Nucleotide sequences are operably linked to a regulatory sequence when the regulatory sequence is functionally associated with the DNA sequences. Thus, a promoter nucleotide sequence is operably linked to a DNA sequence if the promoter nucleotide sequence controls the transcription of the DNA sequence. An origin of replication that confers the ability to replicate in a host cell, and a selection gene by which transformants are identified are generally incorporated into expression vectors.

As for selectable markers, those commonly used can be routinely used. Examples are genes resistant to antibiotics such as tetracycline, ampicillin, kanamycin, neomycin, hygromycin or spectinomycin and auxotrophic genes such as HIS3, TRP1.

In preferred embodiments of the present invention, two or more DES1 expression vectors carrying mutually different selectable markers may be used for 1) introduction of the sphingoid Δ4-desaturase gene (DES1). For example, in Example 7 described later, when using three expression vectors carrying three different auxotrophic selectable markers, i.e., uracil, tryptophan and lysine markers, the productivity in yeast transformant cells increased nearly twice. Multiple selectable markers to be used are not limited to auxotrophic genes, and desired known selectable markers may be used in combination as appropriate.

Yeast vectors will often contain an origin of replication sequence derived from the 2μ yeast plasmid, an autonomous replication sequence (ARS), a promoter region, a sequence for polyadenylation, a sequence for transcription termination, and a selectable marker gene.

Vectors can be conveniently prepared by routine fusion of a desired gene to a recombination vector available in the art (e.g., plasmid DNA). Methods for integrating a DNA fragment of a gene into a vector such as a plasmid are described in, for example, Sambrook, J., and Russell, D. W. (2001). Molecular Cloning: A Laboratory Manual, 3rd ed. (New York: Cold Spring Harbor Laboratory Press). Commercially available ligation kits (e.g., available from TAKARA) can be conveniently used.

Methods for introducing a vector into a host cell include calcium phosphate or calcium chloride/rubidium chloride transfection, electroporation, electroinjection, chemical treatment with PEG or the like, the use of a gene gun, etc. described in Sambrook, J. et al. (2001) (supra.).

Methods for Abolishing Each Gene by Transformation of Yeast

The methods of the present invention comprise:
2) abolishing the expression of the yeast sphinganine C4-hydroxylase gene (SUR2) by transformation of the yeast cell; and
3) abolishing the expression of the yeast sphingoid base kinase gene (LCB4) by transformation of the yeast cell.

In preferred embodiments, the methods of the present invention further comprise:
4) abolishing the expression of the yeast sphingolipid α-hydroxylase gene (SCS7) by transformation of the yeast cell.

As used herein, the expression "abolishing the expression of each gene" means that the protein activity encoded by each gene is not produced. Any abolishment is included in the scope of the present invention to achieve the purposes in the methods of the present invention, so long as the protein activity encoded by the gene is not exerted eventually, such as disrupting the gene on the genome of a yeast cell, inhibiting the transcription of the gene, inhibiting the translation of the gene into a protein, or inhibiting activity even if it is translated into a protein. Abolishment may be partial or complete. Typically, each gene on the genome of a mother cell is disrupted to partially or completely delete the gene.

The expression of the SUR2, LCB4 and SCS7 genes can be abolished by known methods.

For example, a DNA fragment containing upstream and downstream nucleotide sequences of each gene fused to a selectable marker was used to delete the gene by homologous recombination with the natural genome sequence of yeast in the examples herein below.

Disruption of a gene can be performed by addition or deletion of one or more nucleotides in a region responsible for the expression of a gene product in the target gene, such as a coding region or a promoter region, or by entire deletion of these regions. Such methods for gene disruption can be found in known publications (e.g., see Yeast 10, 1793 (1994), Yeast 15, 1541 (1999), Proc. Natl. Acad. Sci. USA, 76, 4951 (1979), Methods in Enzymology, 101, 202 (1983), etc.).

In addition to gene disruption, other methods for suppressing the expression of each gene for the purposes of the present invention include antisense methods (e.g., see Hirajima and Inoue: New Biochemistry Experiment Course 2 Nucleic acid, IV. Gene Replication and Expression (Japanese Biochemical Society Ed., Tokyo Kagaku Dozin Co., Ltd.) pp. 319-347, 1993, etc.), RNAi methods (see Domestic announcement No. 2002-516062 of PCT application; US Patent Laid-Open Publication No. 2002/086356A; Nature Genetics, 24 (2), 180-183, 2000, etc.), ribozyme methods (see FEBS Lett. 228: 228, 1988; FEBS Lett. 239: 285, 1988; Nucl. Acids. Res. 17: 7059, 1989, etc.), cosuppression (e.g., see Smyth DR: Curr. Biol. 7: R793, 1997, Martienssen R: Curr. Biol. 6: 810, 1996, etc.), etc.

Methods for Verifying Ceramide Synthesis

The human ceramide (ceramide NS) produced by the methods of the present invention can be extracted/purified by using known methods. The methods of the present invention allow large-scale culture and convenient and rapid extraction/purification of the ceramide because yeast cells are used. The purified ceramide can be identified by using known methods for analyzing sphingoid bases. Analytical methods include, e.g., TLC and HPLC as shown in FIG. 4, mass spectrometry (e.g., LC-MS, LC-MS/MS, FT-MS), etc.

ADVANTAGES OF THE INVENTION

According to the methods of the present invention for producing ceramide using yeast transformants, human ceramide highly functional on the human skin can be produced inexpensively.

Figure 1:
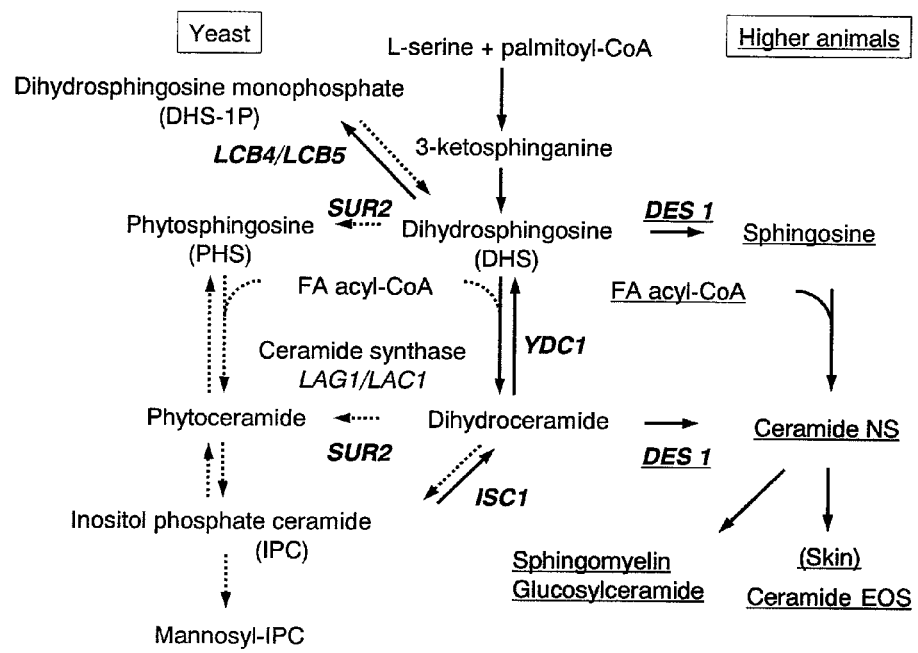
FIG. 1 shows the synthetic/metabolic pathways for sphingolipids in yeast and higher animal cells.
Figure 2:
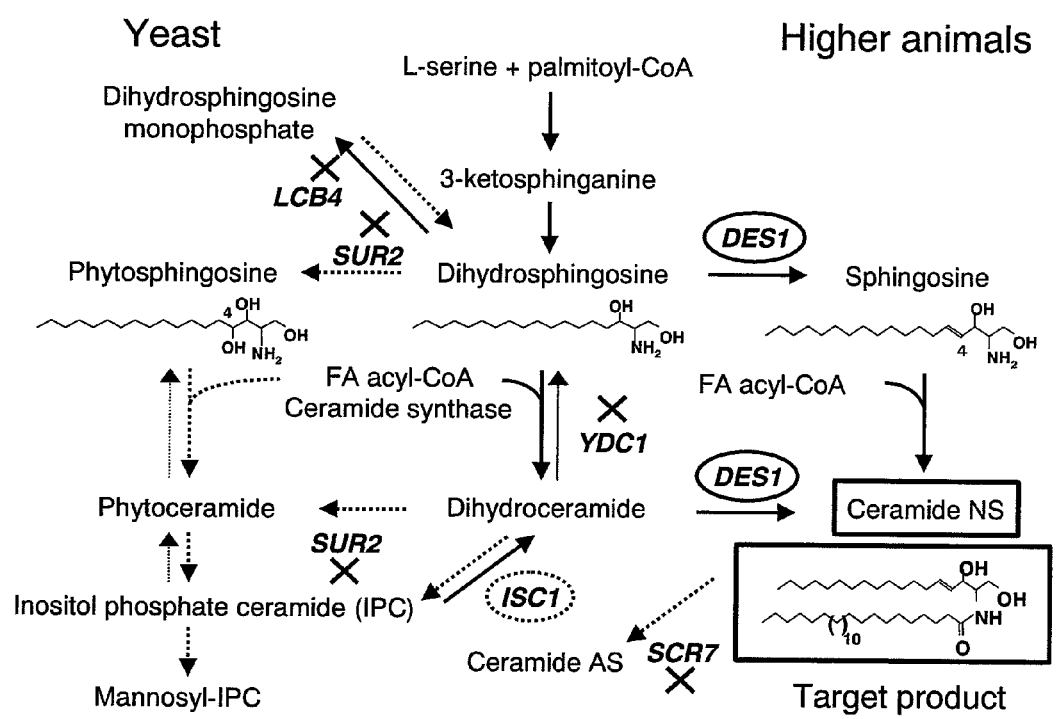
FIG. 2 shows an overview of a preferred embodiment of a method for producing human ceramide in yeast cells according to the present invention.
Figure 3:
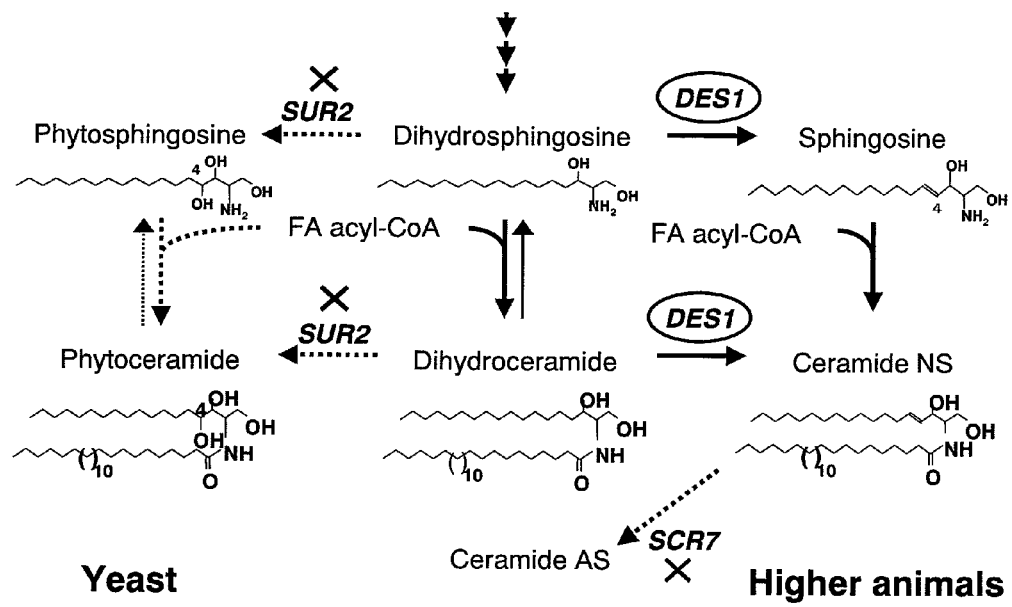
FIG. 3 shows the molecular species of sphingoid bases and ceramides and the structural formulae thereof in yeast and higher animals.

From the left, Samples 1-3 are as follows.

1. SUR2/SCS7 double disruption (Example 3)+empty vector
2. SUR2/SCS7 double disruption (Example 3)+DES1 gene expression
3. SUR2/SCS7/LCB4 triple disruption (Example 4)+DES1 gene expression

EXAMPLES

The following examples further illustrate the present invention but are not intended to limit the technical scope of the invention. Those skilled in the art can readily add modifications/changes to the present invention in the light of the description herein, and those modifications/changes are included in the technical scope of the present invention.

Example 1

Preparation of Expression Vector for Human Sphingoid Δ4-Desaturase Gene (DES1)

Based on the nucleotide sequence of the human sphingoid Δ4-desaturase gene (DES1) (SEQ ID NO: 23, CDS is shown in SEQ ID NO: 1) in a public database (GenBanK™: accession number AF466375), primers des1F (SEQ ID NO: 11) and des1R (SEQ ID NO: 12) were prepared.

```
SEQ ID NO: 11:
5'-CCTTCTCTAGAGGATCCATGGGGAGCCGCGTCTCGCGGGAAG
AC-3'

SEQ ID NO: 12:
5'-CCTTCGAATTCCCCGGGCCAGGGGAGCTTCTGAGCATCACTG
GTC-3'
```

The primer pair was used to perform PCR with a human cDNA library as a template. The resulting PCR product (about 1.1 kb) was cloned into the gene expression vector for yeast pKO11 (Kamei et al., J. Biol. Chem., 273, 28341, 1998; provided by Dr. K. Tanaka) using BamHI and SmaI sites.

The nucleotide sequence of the clone was determined by the Sanger method to confirm that it was identical to the sequence in the database. The clone was subcloned into the gene expression vector for yeast pRS series (p4XX) (Mumberg et al., Gene, 156, 119, 1995) using BamHI and XhoI sites.

Example 2

Preparation of Disruption Strain of Yeast Sphinganine C4-Hydroxylase Gene (SUR2)

Based on a sequence (SEQ ID NO: 3) containing the nucleotide sequence of the yeast sphinganine C4-hydroxylase gene (SUR2) (SEQ ID NO: 5) and its upstream and downstream regions in a public yeast genome database (SGD (Saccharomyces Genome Database, primers sur2F (SEQ ID NO: 13) and sur2R (SEQ ID NO: 14) were prepared.

```
SEQ ID NO: 13:
5'-CTCCGGCTTCTGCGGTTTTTCTTAGTCTTTCCGCACCAATTTTC
ACAGGAATTCCCGGGGATCCGG-3'

SEQ ID NO: 14:
5'-GGATAATAAATACAAACGTGGGAAGTCGGAGACATTGCCTTTAC
CCAGCAAGCTAGCTTGGCTGCAGG-3'
```

The primer pair was used to perform PCR with plasmid pYDp-L (Berben et al., Yeast, 7, 475, 1991) as a template, thereby giving a PCR product containing a 295-bp upstream region of the SUR2 gene, a selectable marker and a 75-bp downstream region of the SUR2 gene fused together. This PCR product was routinely transformed into the strain FK113 (MATa, ura3, his3, leu2, lys2, trp1, bar1-1), and transformants were selected in an auxotrophic medium to give a SUR2 gene disruption strain.

The disruption of the SUR2 gene was confirmed by PCR using confirmation primers designed to be amplified into fragments of different lengths depending on whether the gene is normal or disrupted (SEQ ID NOs: 15 and 16).

```
SEQ ID NO: 15:
5'-CTCCGGCTTCTGCGGTTTTTCTTAGTCTTTC-3'

SEQ ID NO: 16:
5'-GGAAGTCGGAGACATTGCCTTTACCCAG-3'
```

Example 3

Preparation of Double Disruption Strain of Yeast SUR2 and Yeast Sphingolipid α-hydroxylase (SCS7) Genes Based on a sequence (SEQ ID NO: 4) containing the nucleotide sequence of the yeast sphingolipid α-hydroxylase gene (SCS7) (SEQ ID NO: 7) and its upstream and downstream regions in a public yeast genome database (SGD), primers scs7up280F (SEQ ID NO: 17) and scs7up280R_G418 (SEQ ID NO: 18), as well as primers scs7down280F_G418 (SEQ ID NO: 19) and scs7down280R (SEQ ID NO: 20) were prepared.

```
SEQ ID NO: 17:
5'-CGAATTCAGCCGAAAACAGTCTTGCTT-3'

SEQ ID NO: 18:
5'-CTCCATGTCGCTTACCACCGCTTTTAGTGC-3'

SEQ ID NO: 19:
5'-CGCTATACTGCAGCCTCGTCCAAAATTGTCA-3'

SEQ ID NO: 20:
5'-CGAATTCTTGCCAACCTGATCTGTGAA-3'
```

The primer pairs were used to perform PCR with a routinely prepared yeast genomic DNA as a template to give PCR products corresponding to an upstream region of about 280 bp and a downstream region of about 280 bp of the SCS7 gene, respectively.

Next, in the second PCR, these two PCR fragments were mixed and applied to a G-50 gel filtration column (Quick Spin Columns for radiolabeled DNA purification, Roche) to remove the existing primers, and then pFA6a-kanMX4 (EMBL AJ002680) vector having the geneticin (G418) resistance gene as a marker was used as a template to amplify a PCR fragment of about 2.3 kb using a combination of the above primers scs7up280F and scs7down280R. This final PCR product was routinely transformed into the yeast SUR2 disruption strain of Example 2. Transformants were screened on YPD plates (1% yeast extract, 2% polypeptone, 2% glucose, 2% agar) containing 300 mg/L G418 to give a SUR2/SCS7 double disruption strain.

To examine whether the G418 gene was inserted at a desired site and the SCS7 gene was disrupted, primer SCS7 GD CheckF2 (SEQ ID NO: 21) was prepared upstream of the SCS7 gene, while primer G418CheckR (SEQ ID NO: 22) was prepared in the G418 gene. A transformant giving a 1.2-kb fragment by PCR amplification was identified as a gene disruption strain.

```
SEQ ID NO: 21:
5'-GCGCTGCATACATAGACATATACAC-3'

SEQ ID NO: 22:
5'-ATACGCGATCGCTGTTAAAAGGACA-3'
```

Example 4

Preparation of Triple Disruption Strain of Yeast SUR2, Yeast SCS7 and Yeast Sphingosine Kinase (LCB4) Genes Based on the nucleotide sequence of a sequence (SEQ ID NO: 24) containing the sphingosine kinase gene (LCB4) (SEQ ID NO: 9) and its upstream and downstream regions in a public yeast genome database (SGD), primers LCB4.KO-F (SEQ ID NO: 25) and LCB4.KO-R (SEQ ID NO: 26) were prepared in the same manner as shown in Examples 1 to 3. Plasmid pYDp-H carrying His3 as a marker (Berben et al., cited in Example 2) was used as a template for PCR with the above primer pair to amplify a fragment of about 1.2 kb. This PCR product was routinely transformed into the yeast SUR2/SCS7 double disruption strain of Example 3. Transformants were screened on histidine-free complete minimal plates (SC-His) to obtain a SUR2/SCS7/LCB4 triple disruption strain.

```
SEQ ID NO: 25:
5'-AGGTTATCAAGAACACAAAAGTCTAGCAGCGAAAAGTACGGAAT
TCCCGGGGATCCG-3'

SEQ ID NO: 26:
5'-AAGGACGCAACTTCCAAGTGAATGATTTAATGTGCATATATGAA
GCTAGCTTGGCTGCAG-3'
```

Gene disruption was confirmed by PCR with primers LCB4.KOC-F (SEQ ID NO: 27) and LCB4.KOF-R (SEQ ID NO: 28) which were designed to be amplified by PCR into fragments of different lengths depending on whether the gene is normal or disrupted.

```
SEQ ID NO: 27:
5'-GAAGAAAGGCATACAAGAAGGTGAAAATTCG-3'

SEQ ID NO: 28:
5'-TCTGGATAAAGAGAGTACGACTTCTAAGG-3'
```

Example 5

Preparation of Two Vectors Carrying Tryptophan and Lysine, Respectively, as an Auxotrophic Marker in Place of Uracil in Human DES1 Expression Vector From the hDES1 expression vector (phDES1) of Example 1, a hDES1 gene fragment of about 1.3 kb including the promoter and terminator was excised by digestion with BamHI and XhoI, and inserted into the same sites of pRS424 (2μ)GPD vector carrying Trp1 as a marker (Mumberg et al., GENE, 156, 119-122, 1995) to construct a hDES1 expression vector carrying a tryptophan marker (phDES1w).

Based on a nucleotide sequence (SEQ ID NO: 29) containing the α-aminoadipate reductase gene (LYS2) and its upstream and downstream regions in SGD, primers LYS2-PstI-F (SEQ ID NO: 30) and LYS2-SmaI-R (SEQ ID NO: 31) were prepared for LYS2 cloning in the same manner as shown in Examples 1 to 4. A routinely prepared yeast genomic DNA was used as a template for PCR with the above primers to amplify a fragment of about 5.1 kb. The resulting fragment was subcloned into pCR-Blunt II-TOPO vector and then digested with restriction enzymes PstI and SmaI to excise a Lys2 fragment of about 5.1 kb, which was then inserted in place of the Ura3 marker in phDES1 of Example 1 which had been digested with PstI and NaeI to remove the marker, thereby constructing a hDES1 expression vector carrying a lysine marker (phDES1k).

```
SEQ ID NO: 30:
5'-ACTGCAGAATTCCGGCGGTTTTTCGCGTG-3'

SEQ ID NO: 31:
5'-ACCCGGGGATTTGTCTCAACCTGCTTTGG-3'
```

Example 6

Preparation of Yeast SUR2/SCS7/LCB4 Triple Disruption Strain Carrying Expression Plasmid for Human DES1

The expression vector for human DES1 (hDES1) prepared in Example 1 (phDES1) as well as phDES1w and phDES1k prepared in Example 5 were transformed into the yeast SUR2/SCS7/LCB4 triple disruption strain.

Transformation was performed in a routine manner. Transformants were screened on uracil-free complete minimal plates (SC-Ura) for expression of phDES1 alone and on uracil-, tryptophan- and lysine-free complete minimal plates (SC-Ura,Trp,Lys) for co-expression of phDES1, phDES1w and phDES1k.

Example 7

Analysis of Sphingoid Bases in Yeast Transformant Strains of Ceramide Synthetic/Metabolic System Carrying Expression Plasmids for Human DES1

The following strains:
(1) parent strain FK113;
(2) human DES1 gene-expressing yeast (phDES1) SUR2/SCS7/LCB4 triple disruption strain obtained in Example 6; and
(3) human DES1 gene-expressing yeast (phDES1, phDES1w, phDES1k) SUR2/SCS7/LCB4 triple disruption strain
were each cultivated in SC medium at 30° C. for 24 hours. Then, they were incubated under heat shock conditions at 37° C. for 90 minutes, and sphingoid bases were extracted from the cells and derivatized with dinitrophenol as described in a publication (Sperling et al., Journal of Biological chemistry, 273, 28590, 1998).

The sphingoid bases were analyzed by thin layer chromatography (TLC) and high-speed liquid chromatography (HPLC). The procedures are briefly described below.

Cells (wet weight 350 mg) were directly hydrolyzed in 3 ml of 1,4-dioxane/water, 1:1 (v/v) containing 10% (w/v) Ba(OH)$_2$ at 110° C. for 24 hours. Released sphingoid bases were extracted by separation into layers with chloroform/1,4-dioxane/water, 8:3:8 (v/v/v). The organic layers were washed with equal amounts of 0.1 M KOH and 0.5 M KCl, and then reacted with 0.2 ml of a 0.5% (v/v) solution of 1-fluoro-2,4-dinitrobenzene in methanol and 0.8 ml of 2M borate/KOH (pH 10.5) at 60° C. for 30 minutes to derivatize the sphingoid bases with dinitrophenol (DNP-derivatization). After the reaction, the resulting organic layers were dried in vacuo and the resulting DNP-derivatized sphingoid bases were dissolved in chloroform and then developed with chloroform/methanol, 9:1 (v/v) on silica gel 60 TLC plates. The DNP-derivatized sphingoid bases were observed as yellow spots (dark bleu under UV radiation).

Then, the DNP-derivatized sphingoid bases were recovered from the TLC plates and extracted with chloroform/methanol, 2:1 (v/v), and then separated into layers with chloroform/methanol/0.1 M KOH, 2:1:1 (v/v/v). The resulting organic layers were dried in vacuo, and then dissolved in methanol to prepare HPLC samples. HPLC was performed on a silica gel ODS column, eluting with a linear gradient of 80% methanol/acetonitrile/2-propanol (10:3:1, v/v/v) and 20% water to 0% water (flow rate 1 ml/min, 40 min), and UV absorption at 350 nm was monitored.

Figure 4:
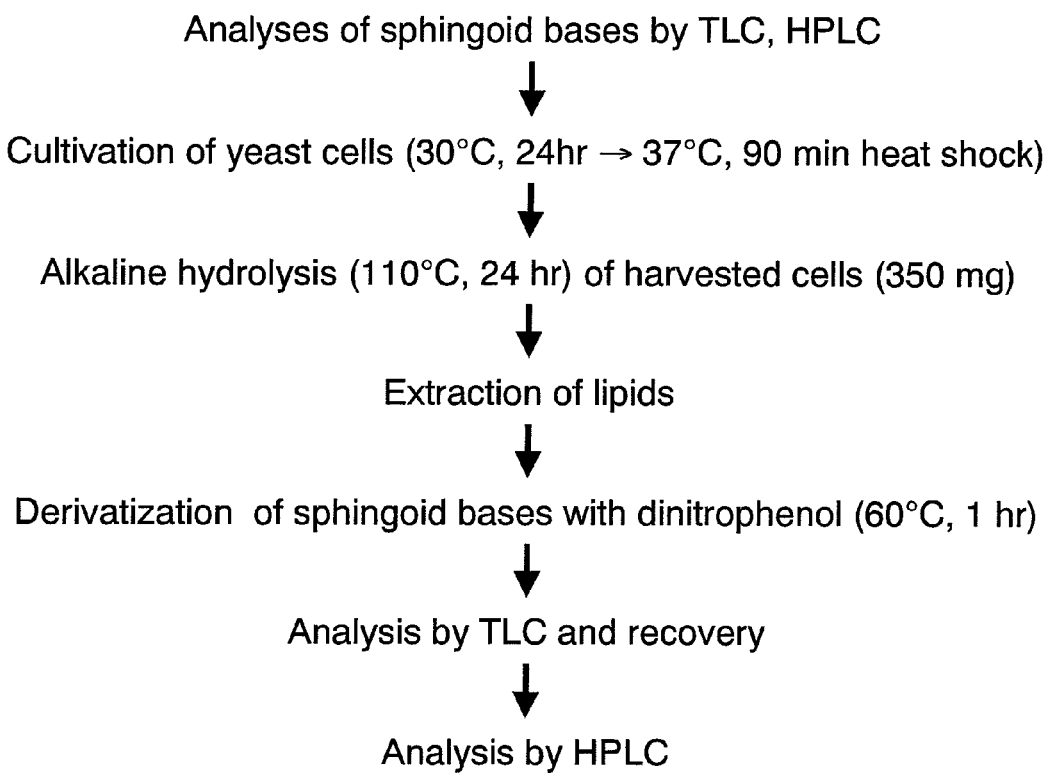
FIG. 4 schematically shows steps from cultivation of yeast cells to analyses by TLC and HPLC.

For easier understanding, a scheme for analyses of sphingoid bases by TLC and HPLC is shown in FIG. 4.

The amounts of sphingosine in cells were determined on the basis of the HPLC data obtained by similarly analyzing a predetermined amount of a synthetic sphingosine purchased from Sigma. The calculated amounts of sphingosine accumulated in 100 mg of cells were as follows:

(1) parent strain FK113: 0.13 μg;
(2) human DES1 gene-expressing yeast (phDES1) SUR2/SCS7/LCB4 triple disruption strain: 27.6 μg; and
(3) human DES1 gene-expressing yeast (phDES1, phDES1w, phDES1k) SUR2/SCS7/LCB4 triple disruption strain: 46.2 μg.

Example 8

Ceramide Analysis Using Tritiated (3H) D-erythro-dihydrosphingosine

The yeast transformants of ceramide synthetic pathway genes described above were cultivated in liquid minimal medium at 25° C. with shaking at 150 rpm for 23 hours, and then the yeast cells were harvested and suspended in liquid minimal medium to prepare 0.5 ml suspensions (16 OD$_{600}$ units/ml). Each suspension was incubated with 10 μl (10 μCi) of tritiated (3H) D-erythro-dihydrosphingosine overnight at 25° C. (Zanolari et al., The EMBO Journal, 19, 2824, 2000). The reaction was quenched with 200 μl of 250 mM NaF and 250 mM NaN$_3$, and then washed three times with ice-cooled sterilized water, and the cells were suspended in 66 μl of sterilized water.

The suspension was vigorously stirred with glass beads to disrupt the cells. Lipids were extracted by adding chloroform and methanol in a ratio of chloroform:methanol:suspension of 10:10:3. The extracts were centrifuged and the resulting supernatants were collected and concentrated/dried by blowing with nitrogen gas. The samples were dissolved in 100 μl of chloroform-methanol-water (10:10:3), and reacted with 20 μl of a 0.6 N solution of NaOH in methanol at 30° C. for 90 min, and then neutralized with a 0.6 N acetic acid solution. The reaction solution was desalted by butanol extraction, and the resulting butanol layer (upper layer) was concentrated/dried by blowing with nitrogen gas.

Figure 5:
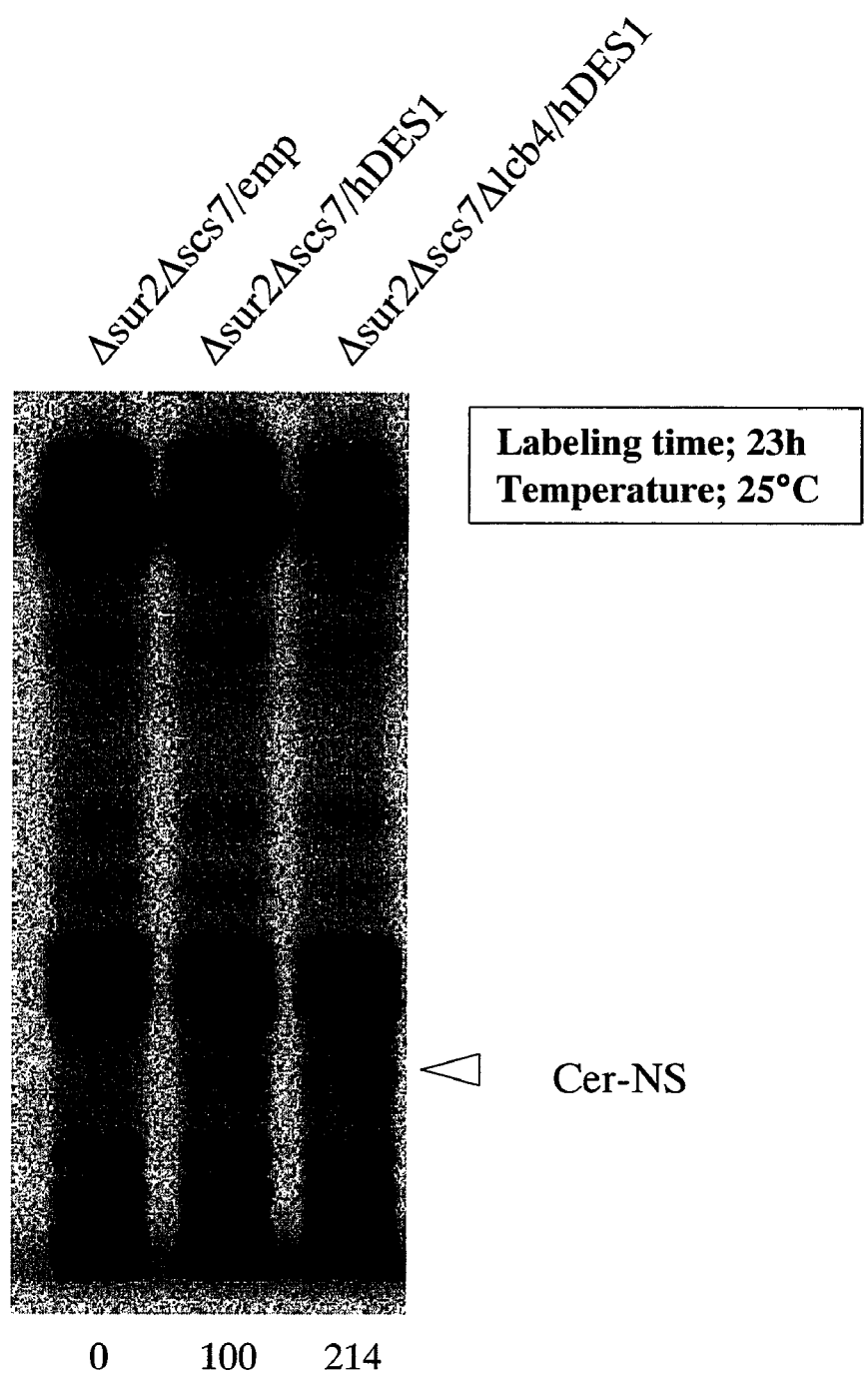
FIG. 5 shows the results of TLC analysis of yeast ceramides using tritiated ($^3$H) D-erythro-dihydrosphingosine and the results of quantification of radioactively labeled ceramides using a Bioimage Analyzer (BAS). Tritiation was performed for 23 hours at a temperature of 25° C.

The lipids were dissolved in 20 μA of chloroform-methanol (1:1), spotted on borate-impregnated thin layer chromatography (TLC) plates, and developed with chloroform-methanol (9:1) (Triola et al., Molecular Pharmacology, 66, 1671, 2004). After the development, radioactively labeled ceramides were analyzed by a Bioimage Analyzer (BAS). The results are shown in FIG. 5.

When DES1 gene is not expressed in the SUR2/SCS7 double disruption strain, ceramide NS (CerNS) was not observed at all (0%). Assuming that ceramide NS (CerNS) in the human DES1-expressing yeast SUR2/SCS7 double disruption strain was 100%, ceramide NS (CerNS) in the human DES1 gene-expressing yeast SUR2/SCS7/LCB4 triple disruption strain was found to be 214%.

The invention claimed is:

1. A method for producing human ceramide in a *Saccharomyces cerevisiae* cell, which comprises:

1) introducing the sphingoid Δ4-desaturase gene (DES 1) by transformation of the *S. cerevisiae* cell with an expression vector encoding said DES1 gene, wherein the sphingoid Δ4-desaturase gene (DES 1) encodes a protein having the amino acid sequence of SEQ ID NO: 2 or an amino acid sequence which has an identity of 90% or more to the amino acid sequence of SEQ ID NO: 2, and having sphingoid Δ4-desaturase activity;

2) abolishing the expression of the yeast sphinganine C4-hydroxylase gene (SUR2-) by transformation of the *S. cerevisiae* cell, wherein the yeast sphinganine C4-hydroxylase gene (SUR2) encodes a protein having the amino acid sequence of SEQ ID NO: 6 or an amino acid sequence which has an identity of 90% or more to the amino acid sequence of in SEQ ID NO: 6, and having sphinganine C4-hydroxylase activity;
3) abolishing the expression of the yeast sphingoid base kinase gene (LCB4) by transformation of the yeast S. cerevisiae cell, wherein the yeast sphingoid base kinase gene (LCB4) encodes a protein having the amino acid sequence of SEQ ID NO: 10 or an amino acid sequence which has an identity of 90% or more to the amino acid sequence of SEQ ID NO: 10, and having sphingoid base kinase activity; and
4) abolishing the expression of the yeast sphingolipid α-hydroxylase gene (SCS7) by transformation of the S. cerevisiae cell, wherein the yeast-sphingolipid α-hydroxylase gene (SCS7) encodes a protein having the amino acid sequence of SEQ ID NO: 8 or an amino acid sequence which has an identity of 90% or more to the amino acid sequence of SEQ ID NO: 8, and having sphingolipid α-hydroxylase activity; wherein said steps of abolishing the expression of genes are conducted by a process independently selected from the group consisting of:

(a) transforming the S. cerevisiae cell with a DNA fragment containing upstream and downstream nucleotide sequences of each gene fused to a selectable marker, thereby the natural genome sequence of said gene in the yeast is replaced with said DNA fragment through homologous recombination;
(b) transforming the S. cerevisiae cell with a vector that inserts or deletes one or more nucleotides in a coding or non-coding region responsible for expression of said genes; and
(c) transforming the S. cerevisiae cell with a vector which produces a nucleotide which suppresses expression of said genes by an antisense method, an RNAi method, a ribozyme method, or cosuppression.

2. The method according to claim 1, wherein two or more DES1 expression vectors carrying mutually different selectable markers are used for introduction of the sphingoid Δ4-desaturase gene (DES1).

* * * * *